(12) United States Patent
Siber

(10) Patent No.: US 7,892,563 B2
(45) Date of Patent: Feb. 22, 2011

(54) METHODS FOR TREATMENT OF SEVERE ACUTE RESPIRATORY SYNDROME (SARS)

(75) Inventor: George R. Siber, Irvington, NY (US)

(73) Assignee: Wyeth Holdings Corporation, Madison, NJ (US)

( * ) Notice: Subject to any disclaimer, the term of this patent is extended or adjusted under 35 U.S.C. 154(b) by 837 days.

(21) Appl. No.: 10/441,059

(22) Filed: May 20, 2003

(65) Prior Publication Data

US 2004/0235047 A1 Nov. 25, 2004

(51) Int. Cl.
*A61K 39/215* (2006.01)
*A61K 39/395* (2006.01)

(52) U.S. Cl. .................. 424/221.1; 424/145.1; 435/335

(58) Field of Classification Search ................ 424/85.1, 424/143.1, 144.1, 145.1, 152.1, 158.1; 514/1, 514/44
See application file for complete search history.

(56) References Cited

U.S. PATENT DOCUMENTS

| | | |
|---|---|---|
| 4,376,110 A | 3/1983 | David et al. |
| 4,699,880 A | 10/1987 | Goldstein |
| 5,096,906 A | 3/1992 | Mandell et al. |
| 5,118,500 A | 6/1992 | Hänel et al. |
| 5,196,430 A | 3/1993 | Mandell et al. |
| 5,395,760 A | 3/1995 | Smith et al. |
| 5,508,300 A | 4/1996 | Duplantier |
| 5,547,979 A | 8/1996 | Christensen, IV et al. |
| 5,563,143 A | 10/1996 | Cohan et al. |
| 5,594,106 A | 1/1997 | Black et al. |
| 5,596,013 A | 1/1997 | Duplantier |
| 5,605,690 A | 2/1997 | Jacobs et al. |
| 5,635,350 A | 6/1997 | Eberle et al. |
| 5,656,272 A | 8/1997 | Le et al. |
| 5,691,382 A | 11/1997 | Crimmin et al. |
| 5,747,514 A | 5/1998 | Beckett et al. |
| 5,795,859 A | 8/1998 | Rathjen et al. |
| 5,821,262 A | 10/1998 | Crimmin et al. |
| 5,824,519 A | 10/1998 | Norris et al. |
| 5,834,485 A | 11/1998 | Dyke et al. |
| 5,861,510 A | 1/1999 | Piscopio et al. |
| 5,863,949 A | 1/1999 | Robinson et al. |
| 5,872,146 A | 2/1999 | Baxter et al. |
| 5,883,131 A | 3/1999 | Burgess et al. |
| 6,036,978 A | 3/2000 | Gombotz et al. |
| RE36,755 E | 6/2000 | Smith et al. |
| 6,080,580 A | 6/2000 | Baker et al. |
| 6,083,534 A | 7/2000 | Wallach et al. |
| 6,107,273 A | 8/2000 | Jameson et al. |
| 6,114,517 A | 9/2000 | Monia et al. |
| 6,277,969 B1 | 8/2001 | Le et al. |
| 6,419,934 B1 * | 7/2002 | Tobinick ............... 424/400 |
| 2001/0021380 A1 | 9/2001 | Pluenneke |

FOREIGN PATENT DOCUMENTS

| | | |
|---|---|---|
| EP | 0 125 023 A1 | 11/1984 |
| EP | 0 171 496 B1 | 2/1986 |
| EP | 0 173 494 A2 | 3/1986 |
| EP | 0 184 187 A2 | 6/1986 |
| EP | 0 212 489 A2 | 3/1987 |
| EP | 0 218 868 A2 | 4/1987 |
| EP | 0 288 088 A2 | 10/1988 |
| EP | 0 308 378 A2 | 3/1989 |
| EP | 0 398 327 A1 | 11/1990 |
| EP | 0 412 486 A1 | 2/1991 |
| EP | 0 433 900 A1 | 6/1991 |
| EP | 0 492 448 A1 | 7/1992 |
| EP | 0 526 905 A2 | 2/1993 |
| EP | 0 516 785 B1 | 2/1996 |
| GB | 2 291 422 A | 1/1996 |
| WO | WO 86/01533 | 3/1986 |
| WO | WO 86/02269 | 4/1986 |
| WO | WO 88/04300 | 6/1988 |
| WO | WO 88/09810 | 12/1988 |
| WO | WO 90/11364 | 10/1990 |
| WO | WO 91/02078 | 2/1991 |
| WO | WO 92/07076 | 4/1992 |
| WO | WO 92/13095 | 8/1992 |
| WO | WO 96/00215 | 1/1996 |
| WO | WO 96/01825 | 1/1996 |
| WO | WO 98/17281 | 4/1998 |
| WO | WO 98/30213 | 7/1998 |
| WO | WO 98/50347 | 11/1998 |
| WO | WO 98/54366 | 12/1998 |
| WO | WO 99/04001 | 1/1999 |
| WO | WO 99/15524 | 4/1999 |
| WO | WO 99/18095 | 4/1999 |
| WO | WO 99/49830 | 10/1999 |
| WO | WO 99/56764 | 11/1999 |
| WO | WO 99/66936 | 12/1999 |
| WO | WO 00/09150 | 2/2000 |
| WO | WO 01/30360 | * 5/2001 |

OTHER PUBLICATIONS

Zhang et al (Infection and Immunity 72:4410-4415, Aug. 2004) (abstract only cited).*
Wong et al (Clinical and Experimental Immunology 136:95-103, Apr. 2004) (abstract only cited).*
Ng et al (Pediatrics 113:pe7-14, Jan. 2004).*

(Continued)

*Primary Examiner*—Gary B. Nickol
*Assistant Examiner*—Elly-Gerald Stoica
(74) *Attorney, Agent, or Firm*—Hunton & Williams LLP

(57) ABSTRACT

Compositions and methods for treating Severe Acute Respiratory Syndrome (SARS) are disclosed herein. Inhibitors of SARS-associated inflammatory cytokines are provided herein for use in treating SARS, including SARS-associated coronavirus (SARS-CoV) infection. Inhibitors of TNF are disclosed herein, as is the use of said inhibitors for treating SARS, including SARS-CoV. Methods of identifying and screening for said inhibitors are also provided.

9 Claims, No Drawings

OTHER PUBLICATIONS

Wang et al (Chinese journal of tuberculosis and respiratory disease, 26:586-589, Oct. 2003) (abstract only cited).*
Ward et al (Antiviral Therapy 10:263-75, 2005) (abstract only cited).*
So et al (Lancet, 361:1615-1617, May 10, 2003).*
Palladino et al (Nature Reviews Drug Discovery 2:736-746, Sep. 2003).*
Nicholls et al (Lancet 361: 1773-1778, published online May 16, 2003).*
Cheung et al, Induction of proinflammatory cytokines in human macrophages by Influenza A (H5N1)viruses; a mechanism for the unusual severity of human disease?, Lancet, 360, 1831-1837, 2002.*
Nicholls et al, Lung Pathology of fatal severe acute respiratory syndrome, Lancet, 361, 1773-1778, 2003; published on line on May 16, 2003.*
Hooper et al., Alterations in TNF-alpha receptor signaling in Experimental Coronavirus Retinopathy, Invest Ophtamol Vis Sci, 45, Suppl., Meeting abstract 565-B538, 2004.*
Tobinick E, TNF-alpha Inhibition for potential therapeutic modulation of SARS Coronavirus infection, Curr. Med. Res. Opin., 20, 39-40, 2004.*
Update: Severe Acute Respiratory Syndrome—United States, 2003, M.M.W.R., 52(17):388-90 (May 2, 2003).
Preliminary Clinical Description of Severe Acute Respiratory Syndrome, M.M.W.R., 52(12):255-256 (Mar. 28, 2003).
Poutanen et al., *New England Journal of Medicine*, Mar. 31, 2003, LOW-1-LOW11, www.nejm.org.
Rota, P.A., et al., Research Articles, Character of Novel Coronavirus Associated with Severe Acute Respiratory Syndrome, May 30, 2003, vol. 300, Science, www.sciencemag.org, pp. 1394-1399.
Marra, M.A., et al., The Genome Sequence of the SARS-Associated Coronavirus, May 30, 2003, vol. 300, Science, www.sciencemag.org, pp. 1399-1404.
D. Cyranoski, Critics slam treatment for SARS as ineffective and perhaps dangerous, *Nature*, 423:4, May 1, 2003, p. 4.
Nesmith, Sars Vaccine Will Take "Several Years," Congress Told, *New York Times Syndicate*; Apr. 7, 2003, May 21, 2003, (http://www.nlm.nih.gov/medlineplus/print/news/fullstory_12280.html), pp. 1-2.
Smith et al., The Active Form of Tumor Necrosis Factor Is a Trimer, *J. Biol. Chem*. vol. 262:6951-6954, May 25, 1987.
M. Krigler et al., A Novel Form of TNF/Cachectin Is a Cell Surface Cytotoxic Transmembrane Protein: Ramifications for the Complex Physiology of TNF, Cell, vol. 53, pp. 45-53, Apr. 8, 1988.
Beutler et al., Cachectin and tumor necrosis factor as two sides of the same biological coin, *Nature*, vol. 320, pp. 584-588 Apr. 17, 1986.
Old, Tumor Necrosis Factor (TNF), Science, vol. 230, pp. 630-632.
Le et al., Tumor Necrosis Factor and Interleukin 1: Cytokines with Multiple Overlapping Biological Activities, Laboratory Investigation, vol. 56, No. 3, pp. 234-248, 1987.
Rubin et al., Nonhematopoietic Cells Selected For Resistance To Tumor Necrosis Factor Produce Tumor Necrosis Factor, J. Exp. Med., vol. 164, Oct. 1986, pp. 1350-1355.
Spriggs et al., Induction of tumor necrosis factor expression and resistance in a human breast tumor cell line, Proc. Natl. Acad. Sci., vol. 84, pp. 6563-6566, Sep. 1987.
Cuturi et al., Independent Regulation Of Tumor Necrosis Factor And Lymphotoxin Production By Human Peripheral Blood Lymphocytes, J. Exp. Med., vol. 165, Jun. 1987, pp. 1581-1594.
Sung et al., Production of tumor necrosis factor/cachectin by human B cell lines and tonsillar B cells, J. Exp. Med., vol. 168, Nov. 1988, pp. 1539-1551.
Pober et al., Tow distinct monokines, interleukin 1 and tumor necrosis factor, each independently induce biosynthesis and transient expression of the same antigen on the surface of cultured human vascular endothelial cells[1], The Journal of Immunology, vol. 136, No. 5, Mar. 1, 1986, pp. 1680-1687.
Pober et al., Activation of cultured human endothelial cells by recombinant lymphotoxin: comparison with tumor necrosis factor and interleukin 1 species[1], The Journal of Immunology, vol. 168, No. 10, pp. 3319-3324, May 15, 1987.
Camussi et al., Tumor necrosis factor/cachectin stimulates peritoneal macrophages, polymorphonuclear neutrophils, and vascular endothelial cells to synthesize and release platelet-activating factor, J. Exp. Med., vol. 166, Nov. 1987, pp. 1390-1404.
Cerami et al., The role of cachectin/TNF in endotoxic shock and cachexia, Ommunology Today, vol. 9, No. 1, 1988, pp. 28-31.
Oliff et al., Tumors secreting human TNF/Cachectin induce cachexia in mice, Cell, vol. 50, pp. 555-563, Aug. 14, 1987.
Piguet et al., Tumor necrosis factor/cachectin is an effector of skin and gut lesions of the acute phase of graft-vs-host disease, J. Exp. Med., vol. 166, Nov. 1987, pp. 1280-1289.
Michie et al., Tumor necrosis factor and bacterial sepsis, Br. J. Surg., 1989, vol. 76, July, pp. 670-671.
Debets et al., The role of tumor necrosis factor/cachectin in septic shock, Second Vienna Shock Forum, pp. 463-466.
Simpson et al., Role of tumor necrosis factor in sepsis and acute lung injury, Septic Shock, Critical Care Clinics, vol. 5, No. 1, Jan. 1989, pp. 27-47.
Kornbluth et al., Tumor necrosis factor production by human monocytes is a regulated event: induction of tnf-α-mediated cellular cytotoxicity by endotoxin[1], The Journal of Immunology, vol. 137, No. 8, pp. 2585-2591, Oct. 15, 1986.
Michie et al., Detection of circulating tumor necrosis factor after endotoxin administration, The New England Journal of Medicine, vol. 318, No. 23, pp. 1481-1486.
Revhaug et al., Inhibition of cyclo-oxygenase attenuates the metabolic response to endotoxin in humans, Arch. Surg., vol. 123, Feb. 1988, pp. 162-170.
Waage et al., Association between tumour necrosis factor in serum and fatal outcome in patients with meningococcal disease, The Lancet, Feb. 14, 1987, pp. 355-357.
Hammerle et al., Serum proteins and cytokines for prediction of sepsis?, Second Vienna Shock Forum, pp. 715-718.
Debets et al., Plasma tumor necrosis factor and mortality in critically ill septic patients, Critical Care Medicine, vol. 17, No. 6, pp. 489-494.
Calandra et al., Prognostic values of tumor necrosis factor/cachectin, interleukin-1, interferon-α, and interferon-γ in the serum of patients with septic shock, The Journal of Infectious Diseases, 1990, vol. 161, pp. 982-987.
Eck et al., The structure of tumor necrosis factor-α at 2.6 Å resolution, The Journal of Biological Chemistry, vol. 264, No. 29, Oct. 15, 1989, pp. 17595-17605.
Aderka et al., The possible role of tumor necrosis factor (tnf) and its natural inhibitors, the soluble-tnf receptors, in autoimmune diseases, Israel J. Med. Sci., 1992, vol. 28, pp. 126-130.
Seckinger et al., A human inhibitor of tumor necrosis factor α, J. Exp. Med., vol. 167, Apr. 1988, pp. 1511-1516.
Engelmann et al., A tumor necrosis factor-binding protein purified to homogeneity from human urine protects cells from tumor necrosis factor toxicity, The Journal of Biological Chemistry, vol. 264, No. 20, Jul. 15, 1989, pp. 11974-11980.
Loetscher et al., Molecular cloning and expression of the human 55 kd tumor necrosis factor receptor, Cell, vol. 61, pp. 351-359, Apr. 20, 1990.
Schall et al., Molecular cloning and expression of a receptor for human tumor necrosis factor, Cell, vol. 61, pp. 361-370, Apr. 20, 1990.
Nophar et al., Soluble forms of tumor necrosis factor receptors (TNF-Rs). The cDNA for the type I TNF-R, cloned using amino acid sequence data of its soluble form, encodes both the cell surface and a soluble form of the receptor, The EMBO Journal, vol. 9, No. 10, pp. 3269-3278, 1990.
Engelmann et al., Two tumor necrosis factor-binding proteins purified from human urine, The Journal of Biological Chemistry, vol. 265, No. 3, Jan. 25, 1990, pp. 1531-1536.
Idzerda et al., Human interleukin 4 receptor confers biological responsiveness and defines a novel receptor superfamily, J. Exp. Med., vol. 171, Mar. 1990, pp. 861-873.
Curtis et al., T-cell interleukin 1 receptor cDNA expressed in Chinese hamster ovary cells regulates functional responses to interleukin 1, Proc. Natl. Acad. Sci., vol. 86, pp. 3045-3049, May 1989.

Prywes et al., Mutations in the cytoplasmic domain of EGF receptor affect EGF binding and receptor internalization, The EMBO Journal, vol. 5, No. 9, pp. 2179-2190, 1986.

Chou et al., Human insulin receptors mutated at the ATP-bunding site lack protein tyrosine kinase activity and fail to meditate postreceptor effects of insulin, The Journal of Biological Chemistry, vol. 262, No. 4, Feb. 5, 1987, pp. 1842-1847.

Letsinger et al., Cholesteryl-conjugated oligonucleotides: Synthesis, properties, and activity as inhibitors of replication of human immunodeficiency virus in cell culture, Proc. Natl. Acad. Sci., vol. 86, pp. 6553-6556, Sep. 1989.

Lemaitre et al., Specific antiviral activity of a poly(L-lysine)-conjugated oligodeoxribonucleotide sequence complementary to vesicular stomatitis virus N protein mRNA initiation site, Proc. Natl. Acad. Sci., vol. 84, pp. 648-652, Feb. 1987.

Zon, Oligonucleotide analogues as potential chemotherapeutic agents, Pharmaceutical Research, vol. 5, No. 9, 1988, pp. 539-549.

Been et al., One binding site determines sequence specificity of tetrahymena pre-rRNA self-splicing, trans-splicing, and RNA enzyme activity, Cell, vol. 47, pp. 207-216, Oct. 24, 1996.

Hélène, The anti-gene strategy: control of gene expression by triplex-forming-oligonucleotides, Anti-Cancer Drug Design, 1991, vol. 6, pp. 569-584.

Helene et al., Annals of The New York Academy of Sciences, vol. 660, Antisense Strategies, Control of gene expression by triple helix-forming oligonucleotides, 1992, pp. 27-37.

Maher, DNA triple-helix formation: an approach to artificial gene repressors?, BioEssays, vol. 14, No. 12, Dec. 1992, pp. 807-815.

Stein et al., Physiochemical properties of phosphorothioate oligodeoxynucleotides, Nucleic Acids Research, vol. 16, No. 8, 1988, pp. 3209-3221.

Sarin et al., Inhibition of acquired immunodeficiency syndrome virus by oligodeoxynucleoside methylphosphonates, Proc. Natl. Acad. Sci., vol. 85, pp. 7448-7451, Oct. 1988.

Smithies et al., Insertion of DNA sequences into the human chromosomal β-globin locus by homologous recombination, Nature, vol. 317, Sep. 19, 1985, pp. 230-234.

Thomas et al., Site-directed mutagenesis by gene targeting in mouse embryo-derived stem cell, Cell, vol. 51, pp. 503-512, Nov. 6, 1987.

Thompson et al., Germ line transmission and expression of a corrected HPRT gene produced by gene targeting in embryonic stem cell, Cell, vol. 56, pp. 313-321, Jan. 27, 1989.

Grishok et al., Genetic requirements for inheritance of RNAi in *C. elegans*, Science, vol. 287, Mar. 31, 2000, pp. 2494-2497.

Dernburg et al., Transgene-mediated cosuppression in the *C. elegans* germ line, Genes & Development, vol. 14, pp. 1578-1583, 2000.

Köhler et al., Continuous cultures of fused cells secreting antibody of predefined specificity, Nature, vol. 256, Aug. 7, 1975, pp. 495-497.

Haseloff et al., Simple RNA enzymes with new and highly specific endoribonuclease activities, Nature, vol. 334, Aug. 18, 1988, pp. 585-591v.

Coligan et al., Current Protocols in Immunology, vol. 2.

Cabilly et al., Generation of antibody from immunoglobulin polypetide chains produced in *Escherichia coli*, Proc. Natl. Acad. Sci., vol. 81, pp. 3273-3277, Jun. 1984.

Morrison et al., Chimeric human antibody molecules: mouse antigen-binding domains with human constant region domains, Proc. Natl. Acad. Sci., vol. 81, pp. 6851-6855.

Boullianne et al., Production of functional chimaeric mouse/human antibody, Nature, vol. 312, Dec. 13, 1984, pp. 643-646.

Neuberger et al., A hapten-specific chimaeric IgE antibody with human physiological effector function, Nature, vol. 314, Mar. 21, 1985, pp. 268-270.

Sahagan et al., A genetically engineered murine/human chimeric anitbody retains specificity for human tumor-associated antigen, The Journal of Immunolgy, vol. 137, pp. 1066-1074, No. 3, Aug. 1, 1986.

Liu et al., Chimeric mouse-human IgG1 antibody that can mediate lysis of cancer cells, Proc. Natl. Acad. Sci., vol. 84, pp. 3439-3443, May 1987.

Sun et al., Chimeric antibody with human constant regions and mouse variable regions directed against carcinoma-associated antigen 17-1A, Proc. Natl. Acad. Sci., vol. 84, pp. 214-218, Jan. 1987.

Better et al., *Escherichia coli* secretion of an active chimeric antibody fragment, Science, vol. 240, May 20, 1988, pp. 1041-1043.

Liang et al., Production and characterization of monoclonal antibodies against recombinant human tumor necrosis factor/cachectin, Biochemical and Biophysical Research Communication, vol. 137, No. 2, 1986, pp. 847-854, Jun. 13, 1986.

Meager et al., Preparation and characterization of monoclonal antibodies directed against antigenic antibodies directed against antigenic determinants of recombinant human tumour necrosis factor (rTNF), Hybridoma, vol. 6, No. 3, 1987, pp. 305-311.

Fendly et al., Murine monoclonal antibodies defining neutralizing epitopes on tumor necrosis factor, Hybridoma, vol. 6, No. 4, 1987, pp. 359-370.

Bringman et al., Monoclonal antibodies to human tumor necrosis factors alpha and beta: application for affinity purification, immunoassays and as structural probes, Hybridoma, vol. 6, No. 5, 1987, pp. 489-507.

Hirai et al., Production and characterization of monoclonal antibodies to human tumor necrosis factor, Journal of Immunological Methods, vol. 96, 1987, pp. 57-62.

Möller et al., Monoclonal antibodies to human tumor necrosis factor α: in vitro an in vivo application, Cytokine, vol. 2, No. 3, May 1990, pp. 162-169.

Mathison et al., Participation of tumor necrosis factor in the mediation of gram negative bacterial lipopolysaccharide-induced injury in rabbits, J. Clin. Invest., vol. 81, Jun. 1988, pp. 1925-1937.

Beutler et al., Passive immunization against cachectin/tumor necrosis factor protects mice from lethal effect of endotoxin, Science, vol. 229, Aug. 30, 1985, pp. 869-871.

Tracey et al., Anti-cachectin/TNF monoclonal antibodies prevent septic shock during lethal bacteraemia, Nature, vol. 330, Dec. 17, 1987, pp. 662-664.

Shimamoto et al., Monoclonal antibodies against human recombinant tumor necrosis factor: prevention of endotoxin shock, Immunology Letters, vol. 17, 1988, pp. 311-318.

Silva et al., Prophylactic and therapeutic effects of a monoclonal antibody to tumor necrosis factor-α in experimental gram-negative shock, The Journal of Infectious Diseases, 1990, vol. 162, pp. 421-427.

Opal et al., Efficacy of monoclonal antibody directed against tumor necrosis factor in protecting neutropenic rats from lethal infection with *Pseudomonas aeruginosa*, The Journal of Infectious Diseases, 1990, vol. 161, pp. 1148-1152.

Hinshaw et al., Survival of primates in $LD_{100}$ septic shock following therapy with antibody to tumor necrosis factor (TNFα).

Eck et al., The structure of tumor necrosis factor-α at 2.6 Å resolution, The Journal of Biological Chemistry, vol. 264, No. 29, Issue of Oct. 15, pp. 17595-17605, 1989.

Wüthrich, NMR of proteins and nucleic acids.

Clore et al., Determination of three-dimensional structures of proteins and nucleic acids in solution by nuclear magnetic resonance spectroscopy, Critical Reveiws in Biochemistry and Molecular Biology, vol. 24, Issue 5, 1989, pp. 479-564.

Cooke et al., Protein structure determination by nuclear magnetic resonance, BioEssays, vol. 8, No. 2, Feb./Mar. 1988, pp. 52-56.

Wüthrich, Protein structure determination in solution by nuclear magnetic resonance spectroscopy, Science, vol. 243, Jan. 6, 1989, pp. 45-50.

Yang et al., Phenotype knockout of HIV type 1 chemokine coreceptor CCR-5 by intrakines as potential therapeutic approach for HIV-1 infection, Proc. Natl. Acad. Sci., vol. 94, pp. 11567-11572, Oct. 1997.

Chen et al., Inactivation of HIV-1 chemokine co-receptor CXCR-4 by a novel intrakine strategy, Nature Medicine, vol. 3, No. 10, Oct. 1997, pp. 1110-1116.

Dillman, Monoclonal antibodies for treating cancer, Annals of Internal Medicine, 1989, vol. 111, pp. 592-603.

Olsnes et al., Immunotoxins—entry into cells and mechanisms of action, Immunology Today, vol. 10, No. 9, 1989, pp. 291-295.

Goodman and Gilman's, The Pharmacological Basis of Therapeutics, Eighth Edition.

Rosenberg et al., Special Report, Observations on the systemic administration of autologous lymphokine-activated killer cells and recombinant interleukin-2 to patients with metastatic cancer, The New England Journal of Medicine, vol. 313, No. 23, pp. 1485-1492.

Kurnick et al., Functional characterization of T lymphocytes propagated from human lung carcinomas, Clinical Immunology and Immunopathology, vol. 38, 1986, pp. 367-380.

Kradin et al., Tumor-derived interleukin-2-dependent lymphocytes in adoptive immunotherapy of lung cancer, Cancer Immunol Immunother, 1987, vol. 24, pp. 76-85.

Kradin et al., Treatment of patients with advanced cancer using tumor-infiltrating lymphocytes and interleukin 2, Transplantation Proceedings, vol. XX, No. 2, Apr. 1988, pp. 336-338.

Espevik et al., A highly sensitive cell line, WEHI 164 clone 13, for measuring cytotoxic factor/tumor necrosis factor from human monocytes, Journal of Immunological Methods, vol. 95, 1986, pp. 99-105.

Harlow et al., Antibodies, A Laboratory Manual, Cold Spring Harbor Laboratory, 1988.

Ausubel et al., Short protocols in molecular biology, Second Edition, A compendium of methods from current protocols in molecular biology, Harvard Medical School.

Kathleen J. Myers, et al., *Antisense Oligonucleotide Blockage of Tumor Necrosis Factor-α in Two Murine Models of Colitis*; The Journal of Pharmacology and Experimental Therapeutics, vol. 304, No. 1 (2003); pp. 411-424.

K. Lea Sewell, et al., *Phase I Trail of ISIS 104838, a 2'-Methoxyethyl Modified Antisense Oligonucleotide Targeting Tumor Necrosis Factor-α*; The Journal of Pharmacology and Experimental Therapeutics, vol. 303, No. 3 (2002); pp. 1334-1343.

Edward Tobinick, *TNF-Alfa Inhibition for Potential Therapeutic Modulation of SARS Coronavirus Infection*; Curr Med Res Opin (2004) posted Dec. 30, 2003; 2 pages.

Calabrese, L.H. *Molecular differences in anticytokine therapies*. Clinical and Experimental Rheumatology. Mar.-Apr. 2003, vol. 21, No. 2, pp. 241-248.

Bonville, et al. *Altered Pathogenesis of Severe Pneumovirus Infection in Response to Combined Antiviral and Specific Immunomodulatory Agents*, Journal of Virology, Jan. 2003, vol. 77, No. 2, pp. 1237-1244.

Appleyard et al, *Inhibition of the Growth of Human Coronavirus 229E by Leupeptin*, The Journal of General Virology Feb. 1985, vol. 66, pp. 363-366.

Biagi et al., *Efficacy of thalidomide therapy for extramedullary relapse of myeloma following allogeneic transplantation*, Bone Marrow Transplantation Dec. 2001, vol. 28, pp. 1145-1150.

Bonavia et al., *Identification of a Receptor-Binding Domain of the Spike Glycoprotein of Human Coronavirus HCoV-229E* Journal of Virology, Feb. 2003, vol. 77, pp. 2530-2538.

Watson, *TNF inhibitors: A review of the recent patent literature*, Current Drugs LTD, GB., Dec. 2002, vol. 5, No. 12, pp. 1151-1161.

Jones B. M. et al., Prolonged disturbances of in vitro cytokine production in patients with severe acute respiratory syndrome (SARS) treated with ribavirin and steroids, *Clin Exp Immunol*, Mar. 2004, vol. 135, No. 3, pp. 467-473.

Wong C. K. et al., Plasma inflammatory cytokines and chemokines in severe acute respiratory syndrome, *Clin Exp Immunol*, Apr. 2004, vol. 136, No. 1, pp. 95-113.

Openshaw P. J., What does the peripheral blood tell you in SARS?, *Clin Exp Immunol*, Apr. 2004, vol. 136, No. 1, pp. 11-12.

Yang W. *The Lancet*, Severe Acute Respiratory Syndrome (SARS): Infection Control, vol. 361, Apr. 19, 2003, p. 1386-87.

Ho, W. *The Lancet*, Guideline on Management of Severe Acute Respiratory Syndrome (SARS), vol. 361, Apr. 9, 2003, p. 1313-1315.

Reng, M. et al., Pumpless Extracorporeal Lung Assist and Adult Respiratory Distress Syndrome, *The Lancet*, vol. 356, Jul. 15, 2000, p. 219-220.

Holmes, K. V. "Coronaviruses" 1197 vol. 1 Fields Virology, Knipe D. M. et al. Eds (4$^{th}$ Ed) Lippincott Williams & Wilkins, 2001) pp. 1187-1197.

Ashraf H., Investigations Continue as SARS Claims More Lives, *The Lancet*, vol. 361, Apr. 12, 2003, p. 1276.

Poon, L. L. M. et al., Rapid Diagnosis of a Coronavirus Associated with Severe Acute Respiratory Syndrome (SARS), *Clinical Chemistry*, Jun. 2003; vol. 49, pp. 953-955.

Ksiazek et al., A Novel Coronavirus Associated with Severe Acute Respiratory Syndrome, *The New England Journal of Medicine*, p. 1953-1966. vol. 348, 2003.

Peiris J. S. M et al., Coronavirus as a Possible Cause of Severe Acute Respiratory Syndrome, *The Lancet*, vol. 361, Apr. 19, 2003, p. 1319-25.

Palladino et al., Anti-TNF-Therapies: The Next Generation, *Nature Reviews Drug Discovery*, vol. 2, Sep. 2003, pp. 736-746.

Martin et al. *Pentoxifylline and severe acute respiratory syndrome (SARS): a drug to be considered*, Med Sci Monit. Jun. 2003;9(6):SR29-34.

*Updated Interim Surveillance Case Definition for Severe Acute Respiratory Syndrome (SARS)*, M.M.W.R. Dispatch, 2003, vol. 52 No. 1 pp. 1-3.

Ross et al. (2002), The Biology of the Macrophage, p. 32, in Burke and Lewis, (ed.), *The Macrophage*, New York: Oxford University Press, pp. 1-72.

Hendrzak et al. (1994), The Role of Macrophages and Macrophage Cytokines in host Resistance to Herpes Simplex Virus, p. 601, in Zwilling and Eisenstein (ed.), *Macrophage-Pathogen Interactions*, New York: Marcel Dekker, pp. 601-617.

Hill (1992), "CD4+ T cells cause multinucleated giant cells to form around *Cryptococcus neoformans* and confine the yeast within the primary site of infection in the respiratory tract." *J. Exp. Med.* 175:1685-1695.

* cited by examiner

METHODS FOR TREATMENT OF SEVERE ACUTE RESPIRATORY SYNDROME (SARS)

FIELD OF THE INVENTION

The present invention relates to compositions and methods for the treatment of Severe Acute Respiratory Syndrome (SARS). Further, the present invention relates to compositions comprising inhibitors of tumor necrosis factor (TNF), including recombinant TNF receptors, small molecules and antibodies, for use in the treatment of SARS.

BACKGROUND OF THE INVENTION

Severe Acute Respiratory Syndrome (SARS) is a respiratory illness that has recently been reported in a number of countries. SARS first arose as a potential threat to human health in late 2002. It has been recognized as a newly emerging infectious disease that is highly contagious with significant morbidity and mortality. Originating in Southeast Asia, the virus has infected approximately 5,663 individuals in 26 countries around the world as of Apr. 30, 2003. *M.M.W.R.,* 52(17):388-90 (May 2, 2003). Of these infections, 372 (approximately 6.6%) have resulted in fatalities. Id. SARS is a significant threat to the health and welfare of the human population worldwide, and efforts are currently underway to develop treatments for the disease.

SARS is generally characterized by an incubation period typically 2-7 days in length, with infected individuals typically exhibiting high fevers, sometimes with accompanying chills, headache, malaise and myalgia. The illness progresses with the onset of a dry, non-productive cough or dyspnea, accompanied by or advancing into hypoxemia. 10-20% of cases require intubation and mechanical ventilation. Furthermore, at the peak of respiratory illness, approximately 50% of infected individuals develop leukopenia and thrombocytopenia. *M.M.W.R.,* 52(12):255-256 (Mar. 28, 2003).

The patterns by which SARS spreads suggests droplet or contact transmission of a viral pathogen. Poutanen et al., *New England Journal of Medicine*, published online Mar. 31, 2003, www.nejm.org. Recently, SARS has been associated etiologically with a novel virus, SARS-associated coronavirus (SARS-CoV), a member of the coronavirus family of enveloped viruses which replicate in the cytoplasm of infected animal host cells. Coronaviruses are generally characterized as single-stranded RNA viruses having genomes of approximately 30,000 nucleotides. Rota, P. A., et al., *Sciencexpress*, Published online May 1, 2003; 10.1126/science. 1085952. Coronaviruses fall into three known groups; the first two groups cause mammalian coronavirus infections, and the third group causes avian coronavirus infections. Id. Coronaviruses are believed to be the causative agents of several severe diseases in many animals, for example, infectious bronchitis virus, feline infectious peritonitis virus and transmissible gastroenteritis virus, are significant veterinary pathogens. Id. These known coronaviruses cause only mild symptoms in humans.

SARS-CoV, has a genome of 29,727 nucleotides in length with 11 Open Reading Frames and a genomic DNA of 41% G-C. Id. Phylogenetic analysis reveals that SARS-CoV represents a new group of coronavirus, distinct from the previously known three groups of Coronavirus. Id. Sequencing of SARS-CoV isolates from infected patients in other locations worldwide confirms this distinct grouping. Marra, M. A., et al., *Sciencexpress*, Published online May 1, 2003; 10.1126/science. 1085953. In contrast to the three known groups, SARS-CoV causes the severe disease in humans described above.

Recent studies have examined the virulence of SARS-CoV. According to the World Health Organization, SARS-CoV is stable in feces at room temperature for at least 1-2 days, and is stable in stool from diarrhea patients for approximately 4 days. Additionally, SARS-CoV was stable in cell-culture supernatant with minimal reduction in virus concentration after 21 days at 4° C. and −80° C., and SARS-CoV lost only one log of virus concentration at stable room temperature for 2 days in cell-culture supernatant. SARS-CoV does demonstrate susceptibility to commonly used disinfectants and fixatives. WHO Data on Stability and Resistance of SARS. However, the data strongly suggest that SARS-CoV is capable of retaining virulence outside of human hosts for protracted periods of time.

In addition to SARS-CoV, other infectious agents are suspected of being implicated in SARS. For example, a human metapneumovirus has also been isolated from patients suffering from SARS. Poutanen et al., *New England Journal of Medicine*, published online Mar. 31, 2003, www.nejm.org. It is possible that a combination of pathogens is responsible for SARS. It is also possible that SARS involves an opportunistic infection by a secondary pathogen or multiple secondary pathogens.

As of Mar. 25, 2003, the U.S. Centers for Disease Control and Prevention stated that "[n]o specific treatment recommendations can be made at this time." CDC SARS Treatment, www.cdc.gov/ncidod/sars/treatment. One therapy currently administered in Hong Kong, a combination of steroids and the antiviral agent ribavirin, has been criticized as ineffective and even dangerous to recipients. D. Cyranoski, *Nature,* 423:4 (2003). Other attempted therapies have included administration of antibiotics or oseltamivir. Poutanen et al., *New England Journal of Medicine*, published online Mar. 31, 2003, www.nejm.org. In the absence of an effective treatment, healthcare workers are limited to using supportive measures, such as intravenous (IV) fluids, oxygen and, when necessary, mechanical ventilation and intubation, to treat patients having SARS.

Various measures have been attempted in an effort to control the spread of SARS. These measures include travel restrictions/advisories, quarantines, SARS-specific screening in health care settings and increased education of the public regarding proper infection-control procedures. Precautions such as respirators, gloves, goggles and gowns are being recommended for clinicians and health care workers to help limit the spread of SARS. While a few countries have reported that the spread of the disease has peaked, in other countries, such as China, SARS continues to spread uncontrollably.

Experts predict that a vaccine for the disease is unlikely to be available for a number of years. Indeed, according to the top infectious disease scientist for the United States government, "several years" of accelerated research will be required before a vaccine is generally available. Nesmith, New York Times Syndicate; Published online Apr. 7, 2003; www.nlm-.nih.gov/medlineplus/print/news/full story_12280.html Further, the ability of coronaviruses to rapidly mutate could provide a substantial obstacle to the development of an effective vaccine. Moreover, even if a vaccine is developed, the vaccine may comprise the immunity of a patient and actually worsen the immune response to SARS. Thus, the disease remains a significant threat to the world population and appears likely to do so for quite some time.

Accordingly, a need exists for an effective treatment for patients diagnosed with SARS, patients infected with an infectious agent associated with SARS, such as patients infected with SARS-CoV, or patients at imminent risk of contracting SARS, such as individuals that were exposed, or probably will be exposed in the near future, to an infectious agent associated with SARS.

SUMMARY OF THE INVENTION

Provided herein are compositions and methods for treating Severe Acute Respiratory Syndrome (SARS).

An embodiment of the present invention provides a composition comprising: a therapeutically effective amount of an inhibitor of a SARS-associated inflammatory cytokine in a pharmaceutically acceptable carrier.

A further embodiment of the present invention provides a composition comprising: a soluble recombinant SARS-associated inflammatory cytokine receptor, an antibody to a SARS-associated inflammatory cytokine, a small molecule that affects the activity of a SARS-associated inflammatory cytokine, a SARS-associated antisense oligonucleotide or a combination thereof.

An even further embodiment of the present invention provides a composition comprising: a, first substance selected from the group consisting of a soluble recombinant TNF receptor, an antibody to TNF, a small molecule that affects the activity of a TNF, a TNF antisense oligonucleotide and combinations thereof; and a second substance selected from the group consisting of an inhibitor of viral RNA-dependent RNA polymerase, an inhibitor of a virus-encoded protease that affects processing of a viral RNA-dependent RNA polymerase, an inhibitor of coronavirus budding or release from infected cells, inhibitor of coronavirus budding or release from infected cells affects the activity of hemagglutinin-esterase, an inhibitor of virus binding to a specific cell surface receptor, an inhibitor of receptor-induced conformational changes in virus spike glycoprotein that are associated with virus entry and combinations thereof.

Another embodiment of the present invention provides a composition prepared by a process comprising: administering a candidate SARS-associated inflammatory cytokine inhibitor to a group of patients infected by an infectious agent associated with SARS in a randomized placebo-controlled study; monitoring the effectiveness of the candidate SARS-associated inflammatory cytokine inhibitor; and including a therapeutically effective SARS-associated inflammatory cytokine inhibitor so identified in a composition with a pharmaceutically acceptable carrier.

Yet another embodiment of the present invention provides a composition prepared by a process comprising: administering a candidate tumor necrosis factor (TNF)inhibitor to a group of patients infected by an infectious agent associated with Severe Acute Respiratory Syndrome (SARS) in a randomized placebo-controlled study; monitoring the effectiveness of the candidate TNF inhibitor; and including a therapeutically effective TNF inhibitor so identified in a composition with a pharmaceutically acceptable carrier.

A still further embodiment of the present invention provides a method for treating a patient having Severe Acute Respiratory Syndrome (SARS) comprising: administering to the patent a therapeutically effective amount of an inhibitor of a SARS-associated inflammatory cytokine.

An even further embodiment of the present invention provides a method for treating a patient having Severe Acute Respiratory Syndrome (SARS) comprising: administering to the patient a therapeutically effective amount of an inhibitor of TNF.

Another further embodiment of the present invention provides a method of screening for a SARS-associated inflammatory cytokine inhibitor comprising: administering a candidate SARS-associated inflammatory cytokine inhibitor to a group of patients infected by an infectious agent associated with Severe Acute Respiratory Syndrome (SARS) in a randomized placebo-controlled study; and monitoring the effectiveness of the candidate SARS-associated inflammatory cytokine inhibitor to identify a therapeutically effective SARS-associated inflammatory cytokine.

Yet another further embodiment of the present invention is a method of screening for a composition effective in treating a SARS patient comprising: administering a candidate tumor necrosis factor (TNF) inhibitor to a group of patients infected by an infectious agent associated with SARS in a randomized placebo-controlled study; and monitoring the effectiveness of the candidate TNF inhibitor to identify a therapeutically effective TNF inhibitor.

DETAILED DESCRIPTION OF THE INVENTION

The present invention provides compounds, compositions and methods for treating patients, including humans, who are infected by a pathogenic agent associated with SARS, including suspected, probable and confirmed cases of SARS. For purposes of this disclosure, the terms "illness," "disease," "medical condition," "abnormal condition" and the like are used interchangeably with the term "medical disorder" relating to respiratory distress, particular when the distress is caused by a corona virus.

The terms "TNF receptor" and "TNFR" refer to proteins having amino acid sequences which are substantially similar to the native mammalian TNF receptor or TNF binding protein amino acid sequences, and which are capable of binding TNF molecules and inhibiting TNF from binding to cell membrane bound TNFR.

The term "isolated" or "purified", as used in the context of this specification to define the purity of TNFR protein or protein compositions, means that the protein or protein composition is substantially free of other proteins of natural or endogenous origin and contains less than about 1% by mass of protein contaminants residual of production processes. Such compositions, however, can contain other proteins added as stabilizers, carders, excipients or co-therapeutics. TNFR is isolated if it is detectable as a single protein band in a polyacrylamide gel by silver staining.

"Recombinant," as used herein, means that a protein is derived from recombinant (e.g., microbial or mammalian) expression systems. "Microbial" refers to recombinant proteins made in bacterial or fungal (e.g., yeast) expression systems. As a product, "recombinant microbial" defines a protein produced in a microbial expression system which is essentially free of native endogenous substances. Protein expressed in most bacterial cultures, e.g., *E. coli*, will be free of glycan. Protein expressed in yeast may have a glycosylation pattern different from that expressed in mammalian cells.

"Biologically active," as used throughout the specification as a characteristic of TNF receptors, means that a particular molecule shares sufficient amino acid sequence similarity with the embodiments of the present invention disclosed herein to be capable of binding detectable quantities of TNF, transmitting a TNF stimulus to a cell, for example, as a component of a hybrid receptor construct, or cross-reacting with anti-TNFR antibodies raised against TNFR from natural (i.e., nonrecombinant) sources. Preferably, biologically active TNF receptors within the scope of the present invention are capable of binding greater than 0.1 nmoles TNF per nmole receptor, and most preferably, greater than 0.5 nmole TNF per nmole receptor in standard binding assays.

As used herein, the term "antigen binding region" refers to that portion of an antibody molecule which contains the amino acid residues that interact with an antigen and confer on the antibody its specificity and affinity for the antigen. The antibody region includes the "framework" amino acid residues necessary to maintain the proper conformation of the antigen-binding residues.

As used herein, the term "chimeric antibody" includes monovalent, divalent or polyvalent immunoglobulins. A monovalent chimeric antibody is a dimer (HL)) formed by a chimeric H chain associated through disulfide bridges with a chimeric L chain. A divalent chimeric antibody is a tetramer ($H_2L_2$) formed by two HL dimers associated through at least one disulfide bridge. A polyvalent chimeric antibody can also be produced, for example, by employing, a $C_H$ region that aggregates (e.g., from an IgM H chain, or μ chain).

As used herein, the expression "SARS patient" refers to a mammalian patient, such as a human, who is confirmed to have SARS or who may be classified as having a probable or suspected case of SARS based on epidemiological factors. SARS patients include those who are diagnosed with SARS, those who test positive for infection by an infectious agent (pathogen) associated with SARS (e.g., SARS-CoV), those who are suspected of having SARS based on epidemiological factors, or those who are at an imminent risk of contracting SARS (e.g., one who has been exposed or will likely be exposed to SARS in the near future). The term "SARS patient" is used interchangeably herein with the expressions "patient having SARS," "patient infected with SARS," "patient with SARS", "patients suffering from SARS" and other such expressions.

The phrase "therapeutically effective amount," as used herein, refers to the amount to be administered to a mammalian host (preferably human) in each single dose (as part of a series of doses) to at least cause the individual treated to generate a response that reduces the clinical impact of the infection. This may range from a minimal decrease in pathogenic burden to prevention of the infection. Ideally, the treated individual will not exhibit the more serious clinical manifestations of the infection. The dosage amount can vary depending upon specific conditions of the individual. The specific amount to administer can be determined in routine trials or otherwise by means known to those skilled in the art, based upon the guidance provided herein.

As used herein, the phrase "administering a therapeutically effective amount" of a therapeutic agent means that the patient is treated with the agent in an amount and for a time sufficient to induce a sustained improvement over baseline in at least one indicator that reflects the severity of the disorder. An improvement is considered "sustained" if the patient exhibits the improvement on at least two occasions separated by one or more weeks. The degree of improvement is determined based on signs or symptoms, and determinations may also employ questionnaires that are administered to the patient, such as quality-of-life questionnaires. As used herein, the terms "tumor necrosis factor" or "TNF" refer to TNF-α and/or TNF-β.

Cytokines are protein molecules that are released by cells when activated by antigens and are believed to be involved in cell-to-cell communications, acting as enhancing mediators for immune responses through interaction with specific cell-surface receptors on leukocytes. There are various different types of cytokines, including interleukins, lymphokines, interferons and tumor necrosis factor (TNF).

Monocytes and macrophages secrete cytokines known as tumor necrosis factor-α (TNFα) and tumor necrosis factor-β (TNFβ) in response to endotoxin or other stimuli. TNF-α is a soluble homotrimer of 17 kD protein subunits (Smith, et al., *J. Biol. Chem.* 262:6951-6954 (1987)). A membrane-bound 26 kD precursor form of TNF also exists (Kriegler, et al., *Cell* 53:45-53 (1988)). For reviews of TNF, see Beutler, et al., *Nature* 320:584 (1986), Old, *Science* 230:630 (1986), and Le, et al., Lab. invest. 56:234.

Cells other than monocytes or macrophages also make TNF-α. For example, human non-monocytic tumor cell lines produce TNF (Rubin, et al., *J. Exp. Med.* 164:1350 (1986); Spriggs, et al., *Proc. Natl. Acad. Sci. USA* 84:6563 (1987)), $CD^4+$ and $CD^8.+$ peripheral blood T lymphocytes and some cultured T and B cell lines (Cuturi, et al., *J. Exp. Med.* 165: 1581 (1987); Sung, et al., *J. Exp. Med.* 168:1539 (1988)) also produce TNF-α.

TNF causes pro-inflammatory actions which result in tissue injury, such as inducing procoagulant activity on vascular endothelial cells (Pober, et al., *J. Immunol.* 136:1680 (1988)), increasing the adherence of neutrophils and lymphocytes (Pober, et al., *J. Immunol.* 138:3319 (1987)), and stimulating the release of platelet activating factor from macrophages, neutrophils and vascular endothelial cells (Camussi, et al., J. Exp. Med. 166:1390 (1987)).

Recent evidence associates TNF with infections (Cerami, et al., *Immunol. Today* 9:28 (1988)), immune disorders, neoplastic pathologies (Oliff, et al., *Cell* 50:555 (1987)), autoimmune pathologies and graft-versus host pathologies (Piguet, et al., *J. Exp. Med.* 166:1280 (1987)). The association of TNF with cancer and infectious pathologies is often related to the host's catabolic state.

TNF also plays a central role in gram-negative sepsis and endotoxic shock (Michie, et al., *Br. J. Surg.* 76:670-671 (1989); Debets, et al., Second Vienna Shock Forum, p. 463466 (1989); Simpson, et al., *Crit. Care Clin.* 5:27-47 (1989)), including fever, malaise, anorexia, and cachexia. Endotoxin strongly activates monocyte/macrophage production and secretion of TNF and other cytokines (Kornbluth, et al., *J. Immunol.* 137:2585-2591 (1986)). TNF and other monocyte-derived cytokines mediate the metabolic and neurohormonal responses to endotoxin (Michie, et al., *New. Engl. J. Med.* 318:1481-1486 (1988)). Endotoxin administration to human volunteers produces acute illness with flu-like symptoms including fever, tachycardia, increased metabolic rate and stress hormone release (Revhaug, et al., *Arch. Surg.* 123: 162-170 (1988)) Circulating TNF increases in patients suffering from Gram-negative sepsis (Waage, et al., *Lancet* 1:355-357 (1987); Hammerle, et al., Second *Vienna Shock Forum* p. 715-718 (1989); Debets, et al., *Crit. Care Med.* 17:489-497 (1989); Calandra, et al., *J. Infect. Dis.* 161:982-987 (1990)).

Putative receptor binding loci of hTNF has been disclosed by Eck and Sprang (J. Biol. Chem. 264(29), 17595-17605 (1989), who identified the receptor binding loci of TNF-α as consisting of ammo acids 11-13, 3742, 49-57 and 155-157. PCT publication WO91/02078 (1991) discloses TNF ligands which can bind to monoclonal antibodies having the following epitopes: at least one of 1-20, 56-77, and 108-127; at least two of 1-20, 56-77, 108-127 and 138-149; all of 1-18, 58-65, 115-125 and 138-149; all of 1-18, and 108-128; all of 56-79, 110-127 and 135- or 136-155; all of 1-30. 117-128 and 141-153; all of 1-26. 117-128 and 141-153; all of 22-40, 49-96 or 49-97, 11.0-127, and 136-153; all of 12-22, 36-45, 96-105 and 132-157; both of 1-20 and 76-90; all of 22-40, 69-97, 105-128 and 135-155; all of 22-31 and 146-157; all of 22-40 and 49-98; at least one of 22-40, 49-98 and 69-97, both of 22-40 and 70-87.

The numerous biological effects of TNF-α and the closely related cytokine, TNF-β (lymphotoxin), are mediated by two TNF transmembrane receptors, both of which have been cloned. The p55 receptor (also termed TNF-R55, TNF-RI, or TNFR-α) is a 55 kd glycoprotein shown to transduce signals resulting in cytotoxic, antiviral, and proliferative activities of TNF-α. The p75 receptor (also termed TNF-R75, TNF-RII, or -TNFR-α) is a 75 kDa glycoprotein that has also been shown to transduce cytotoxic and proliferative signals as well as signals resulting in the secretion of GM-CSF. For further discussion see, Aderka, et al., Isrl. *J. Med, Sci.* 28:126-130 (1992) (Seckinger, et al., *J. Exp. Med.* 167:1511-1516 (1988); Engelmann, et al., *J. Biol. Chem.* 264:11974-11980 (1989)); Loetscher, et al., *Cell* 61:351-359 (Apr. 20, 1990); Schall et at., *Cell* 61:361-370 (Apr. 20, 1990); Nophar, et al., *EMBO J.* 9 (10):3269-3278 (1990); Engelmann, et at., *J. Biol. Chem.* 265 {3}: 1531-1536 (1990) Engelmann, et al., *J. Biol. Chem.* 264 (20):11974-11980 (1989); European Patent publication number 0 433 900 A1; PCT publication number WO 92/13095; European Patent Publication number 0 526 905 A2; PCT publication WO 92/07076; European Patent Publication 0 412 486 A1; European Patent Publication number 0 398 327 A1; European Patent Publication 0 308 378 A2; U.S. Reissue 36,755; and U.S. Pat. Nos. 5,395,760 and 5,605,690.

The use of inhibitors of TNF for treating a variety of diseases has been disclosed. In particular, in the area of infectious disease, attempts have been made to treat sepsis with inhibitors of TNF. Such attempts to treat sepsis have been unsuccessful. However, inhibitors of TNF are unexpectedly effective in treating the newly emerging infectious disease SARS.

The present invention is directed to compositions that are effective in treating SARS. In particular, the present invention is directed to compounds and compositions for treating SARS, methods of identifying compounds and compositions effective for treating SARS and the use of the present compounds in methods for treating SARS.

In accordance with an implementation, the present invention comprises: a therapeutically effective amount of an inhibitor of a SARS-associated inflammatory cytokine in a pharmaceutically acceptable carrier. Preferably, the inhibitor of the SARS-associated inflammatory cytokine is a soluble recombinant SARS-associated inflammatory cytokine receptor, an antibody to a SARS-associated inflammatory cytokine, a small molecule that affects the activity of a SARS-associated inflammatory cytokine, a SARS-associated antisense oligonucleotide or combinations thereof. More preferably, the inhibitor of the SARS-associated inflammatory cytokine is a soluble recombinant receptor. A SARS-associated inflammatory cytokine receptor inhibitor is preferably identified according to the screening methods of the present invention, as described below. Based upon the guidance provided herein, a person of skill in the art would readily be able to identify such a compound or composition, in accordance with an implementation of the invention.

According to an implementation of the present invention, the present compositions comprise a composition comprising: a therapeutically effective amount of an inhibitor of an inflammatory cytokine in a pharmaceutically acceptable carrier; and a therapeutically effective amount of an anti-viral compound in the pharmaceutically acceptable carrier.

According to another implementation of the invention, the compositions of the invention comprise a first substance selected from the group consisting of a soluble recombinant TNF receptor, an antibody to TNF, a small molecule that affects the activity of a TNF, and a TNF antisense oligonucleotide and combinations thereof. The first substance may be optionally combined with a second substance selected from the group consisting of an inhibitor of viral RNA-dependent RNA polymerase, an inhibitor of a virus-encoded protease that affects processing of a viral RNA-dependent RNA polymerase, an inhibitor of coronavirus budding or release from infected cells, inhibitor of coronavirus budding or release from infected cells affects the activity of hemagglutinin-esterase, an inhibitor of virus binding to a specific cell surface receptor, and an inhibitor of receptor-induced conformational changes in virus spike glycoprotein that are associated with virus entry and combinations thereof.

The compositions of the present invention also contemplate compositions prepared by the process comprising: administering a candidate SARS-associated inflammatory cytokine inhibitor to a group of patients infected by an infectious agent associated with SARS in a randomized placebo-controlled study; and monitoring the effectiveness of the candidate SARS-associated inflammatory cytokine inhibitor. Preferably, the randomized placebo-controlled study is a blind placebo-controlled study or a double blind placebo-controlled study. Also contemplated by the present invention is a composition prepared by the process comprising administering a candidate tumor necrosis factor (TNF) inhibitor to a group of patients infected by an infectious agent associated with Severe Acute Respiratory Syndrome (SARS) in a randomized placebo-controlled study; and monitoring the effectiveness of the candidate TNF inhibitor.

Soluble Recombinant TNF Receptors

According to an embodiment, a composition of the present invention comprises a soluble TNF receptor and preferably a TNFR-Ig. Two distinct types of TNFR are known to exist: Type I TNFR (TNFRI) and Type II TNFR (TNFRII). The mature full-length human TNFRII is a glycoprotein having a molecular weight of about 75-80 kilodaltons (kDa). The mature full-length human TNFRI is a glycoprotein having a molecular weight of about 55-60 kilodaltons (kDa). The preferred TNFRs of the present invention are soluble forms of TNFRI and TNFRII, as well as soluble TNF binding proteins.

Soluble TNFR molecules include, for example, analogs or subunits of native proteins having at least 20 amino acids and which exhibit at least some biological activity in common with TNFRI, TNFRII or TNF binding proteins. Soluble TNFR constructs are devoid of a transmembrane region (and are secreted from the cell) but retain the ability to bind TNF. Various bioequivalent protein and amino acid analogs have an amino acid sequence corresponding to all or part of the extracellular region of a native TNFR.

Equivalent soluble TNFRs include polypeptides which vary from these sequences by one or more substitutions, deletions, or additions, and which retain the ability to bind TNF or inhibit TNF signal transduction activity via cell surface bound TNF receptor proteins. Analogous deletions may be made to muTNFR. Inhibition of TNF signal transduction activity can be determined by transfecting cells with recombinant TNFR DNAs to obtain recombinant receptor expression. The cells are then contacted with TNF and the resulting metabolic effects examined. If an effect results which is attributable to the action of the ligand, then the recombinant receptor has signal transduction activity. Exemplary procedures for determining whether a polypeptide has signal transduction activity are disclosed by Idzerda et. al., *J. Exp. Med.* 171:861 (1990); Curtis et al., *Proc. Natl. Acad. Sci. U.S.A.* 86:3045 (1989); Prywes et al. *EMBO J.* 5:2179 (1986) and Chou et al., *J. Biol. Chem.* 262:1842 (1987). Alternatively, primary cells or cell lines which express an endogenous TNF receptor and have a detectable biological response to "INF could also be utilized.

The nomenclature for TNFR analogs as used herein follows the convention of naming the protein (e.g., TNFR) preceded by either hu (for human) or mu (for murine) and followed by a Δ (to designate a deletion) and the number of the C-terminal amino acid. For example, huTNFRΔ 235 refers to human TNFR having Asp235 as the C-terminal amino acid. In the absence of any human or murine species designation, TNFR refers generically to mammalian TNFR. Similarly, in the absence of any specific designation for deletion mutants, the term TNFR means all forms of TNFR, including mutants and analogs which possess TNFR biological activity.

In a preferred embodiment, the TNFR-Ig is TNFR:Fc, which may be administered in the form of a pharmaceutically acceptable composition as described herein. The diseases described herein may be treated by administering TNFR:Fc one or more times per week by subcutaneous injection, although other routes of administration may be used if desired. In one exemplary regimen for treating adult human patients, 25 mg of TNFR:Fc is administered by subcutaneous injection two times per week or three times per week for one or more weeks, and preferably for four or more weeks. Alternatively, a dose of 5-12 mg/m$^2$ or a flat dose of 50 mg is injected subcutaneously one time or two times per week for one or more weeks. In other embodiments, SARS is treated with TNFR:Fc in a sustained-release form, such as TNFR:Fc that is encapsulated in a biocompatible polymer, TNFR:Fc that is admixed with a biocompatible polymer (such as topically applied hydrogels), and TNFR:Fc that is encased in a semi-permeable implant.

Various other medicaments used to treat the diseases described herein may also be administered concurrently with compositions comprising TNF-α inhibitors, such as TNFR:Fc. Such medicaments include: NSAIDs; DMARDs; analgesics; topical steroids; systemic steroids (e.g., prednisone); other cytokines; antagonists of inflammatory cytokines; antibodies against T cell surface proteins; oral retinoids; salicylic acid; and hydroxyurea. Suitable analgesics for such combinations include: acetaminophen, codeine, propoxphene napsylate, oxycodone hydrochloride, hydrocodone bitartrate and tramadol. DMARDs suitable for such combinations include: azathioprine, cyclophosphamide, cyclosporine, hydroxychloroquine sulfate, methotrexate, leflunomide, minocycline, penicillamine, sulfasalazine, oral gold, gold sodium thiomalate and aurothioglucose. NSAIDs suitable for the subject combination treatments include: salicylic acid (aspirin) and salicylate derivatives; ibuprofen; indomethacin; celecoxib (CELEBREX, Pharmacia and Pfizer); rofecoxib (VIOXX, Merck & Co. Inc.); ketorolac; nambumetone; piroxicam; naproxen; oxaprozin; sulindac; ketoprofen; diclofenac; and other COX-1 and COX-2 inhibitors, propionic acid derivatives, acetic acid derivatives, carboxylic acid derivatives, carboxylic acid derivatives, butyric acid derivatives, oxicams, pyrazoles and pyrazolones, including newly developed anti-inflammatories.

If an antagonist against an inflammatory cytokine is administered concurrently with TNFR:Fc, suitable targets for such antagonists include TGFβ, IL-6 and IL-8.

In addition, TNFR:Fc may be used in combination with topical steroids, systemic steroids, antagonists of inflammatory cytokines, antibodies against T cell surface proteins, methotrexate, cyclosporine, hydroxyurea and sulfasalazine.

An appropriate dose may be determined according to the animal's body weight. For example, a dose of 0.2-1 mg/kg may be used. Alternatively, the dose is determined according to the animal's surface area, an exemplary dose ranging from 0.1-20 mg/m$^2$, or more preferably, from 5-12 mg/m$^2$. For small animals, such as dogs or cats, a suitable dose is 0.4 mg/kg, in a preferred embodiment, TNFR:Fc (preferably constructed from genes derived from the same species as the patient), or another soluble TNFR mimic, is administered by injection or other suitable route one or more times per week until the animal's condition is improved.

TNF antagonist proteins are administered to a mammal, preferably a human, for the purpose of treating SARS. Because of the primary roles, interleukins, for example IL-1, IL-2 and IL-6, play in the production of TNF, combination therapy using TNFR in combination with IL-1R and/or IL-2R may be preferred in the treatment of TNF-associated clinical indications. In the treatment of humans, soluble human TNFR is preferred. Either Type I IL-1R or Type II IL-1R, or a combination thereof, may be used in accordance with the present invention to treat TNF-dependent inflammatory diseases, such as arthritis. Other types of TNF binding proteins may be similarly used.

The subject methods involve administering to the patient a soluble TNF antagonist that is capable of reducing the effective amount of endogenous biologically active TNF, such as by reducing the amount of TNF produced, or by preventing the binding of TNF to its cell surface receptor. Antagonists capable of inhibiting this binding include receptor-binding peptide fragments of TNF, antisense oligonucleotides or ribozymes that inhibit TNF production, antibodies directed against TNF, and recombinant proteins comprising all or portions or receptors for TNF or modified variants thereof, including genetically-modified muteins, multimeric forms and sustained-release formulations.

Preferred embodiments of the invention utilize soluble TNRFs as the TNF antagonist. Soluble forms of TNRs may include monomers, fusion proteins (also called "chimeric proteins"), dimers, trimers or higher order multimers. In certain embodiments of the invention, the soluble TNFR derivative is one that mimics the 75 kDa TNFR or the 55 kDa TNFR and that binds to TNF in the patient's body. The soluble TNFR mimics may be derived from TNFRs p55 or p75 or fragments thereof. TNFRs other than p55 and p75 also are useful for deriving soluble compounds for treating the medical disorders described herein, such as for example the TNFR that is described in WO 99/04001. Soluble TNFR molecules used to construct TNFR mimics include, for example, analogs or fragments of native TNFRs having at least 20 amino acids, that lack the transmembrane region of the native TNFR, and that are capable of binding TNF. Antagonists derived from TNFRs compete for TNF with the receptors on the cell surface, thus inhibiting TNF from binding to cells, thereby preventing it from manifesting its biological activities. Binding of soluble TNFRs to TNF or LT (lymphotoxin-α which is used interchangeably with TNF-β) can be assayed using ELISA or any other convenient assay. This invention provides for the use of soluble TNF receptors in the manufacture of medicaments for the treatment of disease.

The soluble TNFR polypeptides or fragments of the invention may be fused with a second polypeptide to form a chimeric protein. The second polypeptide may promote the spontaneous formation by the chimeric protein of a dimer, trimer or higher order muimer that is capable of binding a TNFα or a LT-α molecule and preventing it from binding to cell-bound receptors. Chimeric proteins used as antagonists include, for example, molecules derived from the constant region of an antibody molecule and the extracellular portion of a TNFR. Such molecules are referred to herein as TNFR-Ig fusion proteins. A preferred TNFR-Ig fusion protein suitable for treating diseases in humans and other mammals is recombinant TNFR:Fc, a term which as used herein refers to "etanercept," which is a dimer of two molecules of the extracellular portion of the p75 TNF-α receptor, each molecule consisting of a 235 amino acid Fc portion of human IgG$_1$. Etanercept is currently sold by Immunex Corporation under the trade name ENBREL™. Because the p75 receptor protein that it incorporates binds not only to TNF-α, but also to the inflammatory cytokine LT-α, etanercept can act as a competitive inhibitor not only of TNF-α, but also of LT-α. This is in contrast to antibodies directed against TNF-α which cannot inhibit LT-α.

Also encompassed by the invention are treatments using a compound that comprises the extracellular portion of the 55 kDa TNFR fused to the Fc portion of IgG, as well as compositions and combinations containing such a molecule. Encompassed also are therapeutic methods involving the administration of soluble TNFRs derived from the extracellular regions of TNF-α receptor molecules other than the p55 and p75 TNFRs, such as for example the TNFR described in WO 99/04001, including TNFR-Ig's derived from this TNFR. Other suitable TNF-α inhibitors include the humanized anti-TNF-α antibody, adalimumab, available under from Abbott Laboratories under the trade name HUMIRA (formerly sold by Knoll Pharmaceutical/BASF under the trade name D2E7). The compositions of the present invention may comprise one or more of the following drugs: infliximab (also known as Remicade (Centocor Inc.), Trocade (Hoffmann-La Roche, RO-32-3555). Leflunomide (also known as Arava from Hoechst Marion Roussel), Kineret (an IL-1 Receptor antagonist also known as Anakinra from Amgen, Inc.).

In one preferred embodiment of the invention, sustained-release forms of soluble TNFRs are used, including sustained-release forms of TNFR:Fc. Sustained-release forms suitable for use in the disclosed methods include, but are not limited to, TNFRs that are encapsulated in a slowly-dissolving biocompatible polymer (such as the alginate microparticles described in U.S. Pat. No. 6,036,978 or the polyethylene-vinyl acetate and poly(lactic-glucolic acid) compositions described in U.S. Pat. No. 6,083,534), admixed with such a polymer (including topically applied hydrogels), and/or encased in a biocompatible semi-permeable implant. In addition, a soluble TNFR type I or type II for use in the herein-described therapies may be conjugated with polyethylene glycol (pegylated) to prolong its serum half-life or to enhance protein delivery.

Small Molecules

Other compounds suitable for treating the diseases described herein include small molecules such as thalidomide or thalidomide analogs, pentoxifylline, or matrix metalloproteinase (MMP) inhibitors or other small molecules. Suitable MMP inhibitors include, for example, those described in U.S. Pat. Nos. 5,883,131, 5,863,949 and 5,861,510 as well as the mercapto alkyl peptidyl compounds described in U.S. Pat. No. 5,872,146. Other small molecules capable of reducing TNF production include, for example, the molecules described in U.S. Pat. Nos. 5,508,300, 5,596,013 and 5,563,143, any of which can be administered in combination with TNF inhibitors such as soluble TNFRs or antibodies against TNF. Additional small molecules useful for treating the TNF-mediated diseases described herein include the MMP inhibitors that are described in U.S. Pat. No. 5,747,514, U.S. Pat. No. 5,691,382, as well as the hydroxamic acid derivatives described in U.S. Pat. No. 5,821,262. The diseases described herein also may be treated with small molecules that inhibit phosphodiesterase IV and TNF production, such as substituted oxime derivatives (WO 96/00215), quinoline sulfonamides (U.S. Pat. No. 5,834,485), aryl furan derivatives (WO 99/18095) and heterobicyclic derivatives (WO 96/0825; GB 2 291 422 A). Also useful are thiazole derivatives that suppress TNF and IFNδ (WO 99/15524), as well as xanthine derivatives that suppress TNF and other proinflammatory cytokines (see, for example, U.S. Pat. No. 5,118,500, U.S. Pat. No. 5,096,906 and U.S. Pat. No. 5,196,430). Additional small molecules useful for treating the hereindescribed conditions include those disclosed in U.S. Pat. No. 5,547,979.

Antisense Oligonucleotides

Also included among the TNF inhibitors of the invention are antisense oligonucleotides that act to directly block the translation of mRNA by hybridizing to targeted mRNA and preventing polypeptide translation. Antisense oligonucleotides are suitable for use in treating any of the medical disorders disclosed herein, either alone or in combination with other TNF inhibitors or in combination with other agents for treating the same condition. Antisense molecules of the invention may interfere with the translation of TNF, a TNF receptor, or an enzyme in the metabolic pathways for the synthesis of TNF. Absolute complementarity, although preferred, is not required. A sequence "complementary" to a portion of a nucleic acid, as referred to herein, means a sequence having sufficient complementarity to be able to hybridize with the nucleic acid, forming a stable duplex (or triplex, as appropriate). The ability to hybridize will depend on both the degree of complementarity and the length of the antisense nucleic acid. Oligonucleotides that are complementary to the 5' end of the message, e.g., the 5' untranslated sequence up to and including the AUG initiation codon, should work most efficiently at inhibiting translation. However, oligonucleotides complementary to either the 5'- or 3'-non-translated, non-coding regions of the targeted transcript can be used. Oligonucleotides complementary to the 5' untranslated region of the mRNA should include the complement of the AUG start codon.

Antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at feast 50 nucleotides. Most preferably, they will contain 18-21 nucleotides.

The backbone of antisense oligonucleotides may be chemically modified to prolong the hall-life of the oligonucleotide in the body. Suitable modifications for this purpose are known in the art, such as those disclosed, tot example, in U.S. Pat. No. 114,517, which describes the use for this purpose of phosphorothioates, phosphorodithioates, phospholriesters, aminoalkylphosphotriesters, methyl and other alkyl phosphonates, various phosphonates, phosphinates, and phosphoramidates and so on.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., 1989, Proc, Natl. Acad. Sci. U.S.A. 86:6553-6556; Lemaitre et. al., 1987, Proc. Natl Acad. Sci. 84:648-652; PCT Publication No. WO88/09810, published Dec. 15, 1988), or hybridization-triggered cleavage agents or intercalating agents. (See, e.g., Zon, 1988, Pharm. Res. 5:539-549). The antisense molecules should be delivered to cells which express the targeted transcript.

Antisense oligonucleotides can be administered parenterally, including by intravenous or subcutaneous injection, or they can be incorporated into formulations suitable for oral administration. A number of methods have been developed for delivering antisense DNA or RNA to cells; e.g., antisense molecules can be injected directly into the tissue or cell derivation site, or modified antisense molecules, designed to target the desired cells (e.g., antisense linked to peptides or antibodies that specifically bind receptors or antigens expressed on the target cell surface) can be administered systemically. However, it is often difficult to achieve intracellular concentrations of the antisense oligonucleotide sufficient to suppress translation of endogenous mRNAs. Therefore a preferred approach utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous target gene transcripts and thereby prevent translation of the targeted mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vestors can be constructed by recombinant DNA technology methods standard in the art. Vectors can be plasmid, viral, or others known in the art, used for replication and expression in mammalian cells. Antisense oligonucleotides for suitable for treating diseases associated with elevated TNF include, for example, the anti-TNF oligonucleotides described in U.S. Pat. No. 6,080,580, which proposes the use of such oligonucleotides as candidates for testing in animal models of diabetes mellitus, rheumatoid arthritis, contact sensitivity, Crohn's disease, multiple sclerosis, pancreatitis, hepatitis and heart transplant.

Ribozyme molecules designed to catalytically cleave mRNA transcripts can also be used to prevent the translation of mRNAs encoding TNF, TNF receptors, or enzymes involved in synthesis of TNF or TNFRs (see. e.g., PCT WO90/11, 364; U.S. Pat. No. 5,824,519). Ribozymes useful for this purpose include hammerhead ribozymes (Haseloff and Gerlach, 1988, *Nature*, 334:585-591), RNA endoribonucleases (hereinafter "Cech-type ribozymes") such as the one that occurs naturally in *Tetrahymena thermophila* (known as the IVS, or L-19 IVS RNA) (see, for example, WO 88/04300; Been and Cech, 1986, *Cell*, 47:207-216). Ribozymes can be composed of modified oligonucleotides (e.g. for improved stability, targeting, etc.) and should be delivered to cells which express the target peptide in vivo. A preferred method of delivery involves using a DNA construct encoding the ribozyme under the control of a strong constitutive pol III or pol II promoter, so that transfected cells will produce sufficient quantities of the ribozyme to destroy endogenous target mRNA, thereby inhibiting its translation.

In accordance with an implementation of the present invention, the antisense molecules contain oligodeoxynucleotide structures complementary to gene sequences in the target virus. Phosphorothioate oligonucleotides that are complementary to viral RNA have demonstrated inhibition of viral replication in cell cultures. ISIS 2922 is a phosphorothioate oligonucleotide with potent antiviral activity against CMV; it is complementary to the RNA of region 2 of the immediate early transcription unit of CMV and inhibits protein synthesis. It is being studied as an intravitre treatment for CMV retinitis. Adverse effects include vitreitis and retinal pigment epithelial stippling.

Alternatively, expression of genes involved in TNF or TNFR production can be reduced by targeting deoxyribonucleotide sequences complementary to the regulatory region of the target gene (i.e., the target gene promoter and/or enhancers) to form triple helical structures that prevent transcription of the target gene. (See, for example, Helene, 1991, *Anticancer Drug Des.*, 6(6), 569-584; Helene, et al., 1992, *Ann. N.Y. Acad. Sci.*, 660, 27-36; and Maher, 1992, Bioassays 14(12), 807-815).

Antisense RNA and DNA, ribozyme, triple helix molecules, etc. of the invention may be prepared by any method known in the art for the synthesis of DNA and RNA molecules, including, for example, solid phase phosphoramidite chemical synthesis. Oligonucleotides can be synthesized by standard methods known in the art, e.g., by use of an automated DNA synthesizer (such as are commercially available from *Biosearch, Applied Biosystems*, etc.). As examples, phosphorothioate oligonucleotides may be synthesized by the method of Stein et al., 1988, *Nucl. Acids Res.* 16:3209, and methylphosphonate oligonucleotides can be prepared as described by Sarin et al., 1988, *Proc. Natl. Acad. Sci. U.S.A.* 85:7448-7451. Alternatively, RNA molecules may generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Endogenous target gene expression can also be reduced by inactivating or "knocking out" the target gene or its promoter using targeted homologous recombination (e.g., see Smithies, et al., 1985, Nature 317, 230-234; Thomas and Capecchi, 1987, *Cell* 51, 503-512; Thompson, et al., 1989, Cell 5, 313-321). For example, a mutant, nonfunctional target gene (or a completely unrelated DNA sequence) flanked by DNA homologous to the endogenous target gene (either the coding regions or regulatory regions of the target gene) can be used, with or without a selectable marker and/or a negative selectable marker, to transfect cells that express the target gene in vivo. Insertion of the DNA construct, via targeted homologous recombination, results in inactivation of the target gene. Such approaches are particularly suited in the agricultural field where modifications to ES (embryonic stem) cells can be used to generate animal offspring with an inactive target gene (e.g., see Thomas and Capecchi, 1987 and Thompson, 1989, supra), or in model organisms such as *Caenorhabditis elegans* where the "RNA interference" ("RNAi") technique (Grishok A, Tabara H, and Mello C C, 2000, *Science* 287 (5462): 2494-2497), or the introduction of transgenes (Dernburg et al., 2000, *Genes Dev.* 14 (13): 1578-1583) are used to inhibit the expression of specific target genes. This approach can be adapted for use in humans provided the recombinant DNA constructs are directly administered or targeted to the required site in vivo using appropriate vectors such as viral vectors.

Anti-TNF Antibodies

Polyclonal antibodies, monoclonal antibodies (mAbs), chimeric antibodies, anti-idiotypic (anti-Id) antibodies to antibodies that can be labeled in soluble or bound form, as well as fragments, regions or derivatives thereon, provided by any known technique, such as, but not limited to enzymatic cleavage, peptide synthesis or recombinant techniques are contemplated by the present invention. Such anti-TNF antibodies of the present invention are capable of binding portions of TNF that inhibit the binding of TNF to TNF receptors.

Polyclonal antibodies are heterogeneous populations of antibody molecules derived from the sera of animals immunized with an antigen. A monoclonal antibody contains a substantially homogeneous population of antibodies specific to antigens, which population contains substantially similar epitope binding sites. mAbs may be obtained by methods known to those skilled in the art. See, for example Kohler and Milstein. Nature 256:495497 (1975); U.S. Pat. No. 4,376,110; Ausubel et al., eds., CURRENT PROTOCOLS IN MOLECULAR BIOLOGY, Greene Publishing Assoc. and Wiley Interscience, N.Y., (1987, 1992); and Harlow and Lane ANTIBODIES: A LABORATORY MANUAL Cold Spring Harbor Laboratory (1988); Colligan et al., eds., Current Protocols in Immunology, Greene Publishing Assoc. and Wiley Interscience, N.Y., (1992, 1993), the contents of which references are incorporated entirely herein by reference. Such antibodies may be of any immunoglobulin class including IgG, IgM, IgE, IgA, GILD and any subclass thereof. A hybridoma producing a mAb of the present invention may be cultivated in vitro, in situ or in vivo. Production of high titers of mAbs in vivo or in situ makes this the presently preferred method or production.

Chimeric antibodies are molecules different portions of which are derived from different animal species, such as those having variable region derived from a murine mAb and a human immunoglobulin constant region, which are primarily used to reduce immunogenicity when administered and to increase yields in production, for example, where murine mAbs have higher yields from hybridomas but higher immunogenicity in humans, such that human murine chimeric mAbs are used. Chimeric antibodies and methods for their production are known in the art (Cabilly et al., *Proc. Natl. Acad. Sci. USA* 81:3273-3277 (1984); Morrison et al., *Proc. Natl. Acad. Sci. USA* 81:6851-6855 (194), Boulianne et al., *Nature* 312: 643-646 (1984); Cabilly et al., European Patent Application 125023 (published Nov. 14, 1984); Neuberger et al., Nature 314:268-270 (1985); Taniguchi et al., European Patent Application 17/496 (published Feb. 19, 1985); Morrison et al., European Patent Application 173494 (published Mar. 5, 1986); Neuberger et al., PCT Application WO 86/01533, (published Mar. 13, 1986); Kudo et al., European Patent Application 184187 (published Jun. 11, 1986); Morrison et al., European Patent Application [73494 (published Mar. 5, 1986); Sahagan et al., *J. Immunol.* 137:1066-1074 (1986): Robinson et al., International Patent Publication #PCT/US86/02269 (published May 7, 1987); Liu et al., *Proc. Natl. Acad. Sci. USA* 84:3439-3443 (1987); Sun et al., *Proc. Nail. Acad. Sci. USA* 84:214-218 (1987); Better et al., *Science* 240:1041-1043 (1988); and Harlow and Lane ANTIBODIES: A LABORATORY MANUAL Cold Spring Harbor Laboratory (1988)).

Polyclonal murine antibodies to TNF are disclosed by Cerami et al (EPO Patent Publication 0212489, Mar. 4, 1987).

Rubin et at. (EPO Patent Publication 0218868, Apr. 22, 1987) discloses murine monoclonal antibodies to human TNF, the hybridomas secreting such antibodies, methods of producing such murine antibodies, and the use of such murine antibodies in immunoassay of TNF.

Yone et al. (EPO Patent Publication 0288088, Oct. 26, 1988) discloses anti-TNF murine antibodies, including mAbs, and their utility in immunoassay diagnosis of pathologies, in particular Kawasaki's pathology and bacterial infection.

Other investigators have described rodent or routine mAbs specific for recombinant human TNF which had neutralizing activity in vitro (Liang, et al., (*Biochem. Biophys. Res. Comm.* 137:847-854 (1986); Meager, et al., Hybridoma 6:305-311 (1987); Fendly et al., Hybridoma 6:359-369 (1987); Bringman, et al. Hybridoma 6:489-507 (1987); Hirai, et al., *J. Immunol. Meth.* 96:57-62. (1987) Moiler, et al., (Cytokine 2:162-169 (1990)).

Neutralizing antisera or mAbs to TNF have been shown in mammals other than man to abrogate adverse physiological changes and prevent death after lethal challenge in experimental endotoxemia and bacteremia. This effect has been demonstrated, e.g., in rodent lethality assays and in primate pathology model systems (Mathison, et al., *J. Clin. Invest.* 81:1925-1937 (1988); Beutler, et al., *Science* 229:869-871 (1985); Tracey, et al., *Nature* 330:662-664 (1987); Shimamoto, et al.,*Immunol. Lett.* 17:311-318 (1988); Silva, et al., *J. Infect. Dis.* 162:421-427 (1990); Opal et al., *J. Infect. Dis.* 161:1148-1152 (1990); Hinshaw, et al., *Circ. Shock* 30:279-292 (1990)).

Anti-TNF antibodies of the present invention can include at least one of a heavy chain constant region ($H_c$) a heavy chain variable region ($H_v$), a light chain variable region ($L_v$) and a light chain constant regions ($L_c$), wherein a polyclonal Ab, monoclonal Ab, fragment and/or regions thereof include at least one heavy chain variable region ($H_v$) or light chain variable region ($L_v$) which binds a portion of a TNF and inhibits and/or neutralizes at least one TNF biological activity.

An antigen is a molecule or a potion of a molecule capable of being bound by an antibody which is additionally capable of inducing an animal to produce antibody capable of binding to an epitope of that antigen. An antigen can have one or more than one epitope.

The specific reaction referred to above is meant to indicate that the antigen will react, in a highly selective manner, with its corresponding antibody and not with the multitude of other antibodies which can be evoked by other antigens. Preferred, antigens that bind antibodies, fragments and regions of anti-TNF antibodies of the present invention include at least 5 amino acids comprising at least one of amino acids residues 87-108 or both residues 59-80 and 8-108 of hTNF-α (of SEQ ID NO:1). Preferred antigens that bind antibodies, fragments and regions of anti-TNF antibodies of the present invention do not include amino acids of amino acids 11-13,3742, 49-57 or 155-157 of hTNF-α (SEQ ID NO: 1).

The epitope is that portion of any molecule capable of being recognized by and bound by an antibody at one or more of the Ab's antigen binding region. Epitopes usually consist of chemically active surface groupings of molecules such as amino acids or sugar side chains and have specific three dimensional structural characteristics as well as specific charge characteristics. By "inhibiting and/or neutralizing epitope" is intended an epitope, which, when bound by an antibody, results in loss of biological activity of the molecule or organism containing the epitope, in vivo, in vitro or in site, more preferably in vivo, including, for example, binding of TNF to a TNF receptor. For instance, such epitopes include those disclosed in U.S. Pat. No. 6,277,969 which is incorporated herein by reference in its entirety.

As used herein, the term "chimeric antibody" includes monovatent, divalent or polyvalent immunoglobulins. A monovalent chimeric antibody is a dimer (HL)) formed by a chimeric H chain associated through disulfide bridges with a chimeric L chain. A divalent chimeric antibody is a tetramer ($H_2L_2$) formed by two HL dimers associated through at least one disulfide bridge. A polyvalent chimeric antibody can also be produced, for example, by employing a $C_H$ region that aggregates (e.g., from an IgM H chain, or μ chain).

Murine and chimeric antibodies, fragments and regions of the present invention comprise individual heavy (H) and/or light (L) immunoglobulin chains. A chimeric H chain comprises an antigen binding region derived from the H chain of a non-human antibody specific for TNF, which is linked to at least a portion of a human H chain C region ($C_H$), such as $CH_1$ or $CH_2$.

A chimeric L chain according to the present invention, comprises an antigen binding region derived from the L chain of a ram-human antibody specific for TNF linked to at least a portion of a human L chain C region ($C_L$).

Antibodies, fragments or derivatives having chimeric H chains and L chains of the same or different variable region binding specificity, can also be prepared by appropriate association of the individual polypeptide chains, according to known method steps, e.g., according to Ausubel infra, Harlow infra, and Colligan infra.

Anti-TNF Immunoreceptor Peptides

Immunoreceptor peptides of this invention can bind to TNF-α and/or TNF-β. The immunoreceptor comprises at least one immunoglobulin heavy or light chain covalently attached to at least a portion of the TNF receptor. In certain preferred embodiments, the heavy chain constant region comprises at least a portion of $CH_1$. Specifically, where a light chain is included with an immunoreceptor peptide, the heavy chain must include the area of $CH_1$ responsible for binding a light chain constant region.

An immunoreceptor peptide of the present invention can preferably comprise at least one heavy chain constant region and in certain embodiments, at least one light chain constant region, with a receptor molecule covalently attached to at least one of the immunoglobulin chains. Light chain or heavy chain variable regions are included in certain embodiments. Since the receptor molecule can be linked within the interior of an immunoglobulin chain, a single chain can have a variable region and a fusion to a receptor molecule.

The portion of the TNF receptor linked to the immunoglobulin molecule is capable of binding TNF-α and/or TNF β. Since the extracellular region of the TNF receptor binds TNF, the portion attached to the immunoglobulin molecule of the immunoreceptor consists of at least a portion of the extracellular region of the TNF receptor.

The immunoglobulin gene can be from any vertebrate source, such as murine, but preferably, it encodes immunoglobulin having a substantial humor of sequences that are of the same origin as the eventual recipient of the immunoreceptor peptide. For example, if a human is treated with a molecule of the invention, preferably the immunoglobulin is of human origin.

TNF receptor constructs for lining to the heavy chain can be synthesized, for example, using DNA encoding amino acids present in the cellular domain of the receptor. Putative receptor binding loci of hTNF have been presented by Eck and Sprange, J. Biol. Chem. 264(29), 17595-17605 (1989), who identified the receptor binding loci of TNF-α as consisting of amino acids 11-13, 37-42, 49-57 and 155-157. PCT application WO91/02078 (priority date of Aug. 7, 1989) discloses TNF ligands which can bind to monoclonal antibodies having the following epitopes of at least one of 1-20, 56-77, and 108-127; at least two of 1-20, 56-77, 108-127 and 138-149; all of 1-18, 5865, 115-125 and 138-149; all of 1-18, 108-128; all of 56 79, 110-127 and 135- or 136-155; all of 1-30 and 117-128 and 141-153; all of 1-26, 117-128 and 141-153; all of 22-40, 49-96 or −97, 11-127 and 136-153; all of 12-22, 36-45, 96-105 and 132-157; all of both of 1-20 and 7690; all of 2240, 69-97, 105-128 and 135-155: all of 22-31 and 146-157; all of 2240 and 49-98; at least one of 22-40, 9-98 and 69-97, both of 2240 and 70-87. Thus, one skilled in the art once armed with the present disclosure, would be able to create TNF receptor fusion proteins using portions of the receptor that are known to bind TNF.

Advantages of using an immunoglobulin fusion protein (immunoreceptor peptide) of the present invention include one or more of (1) possible increased avidity for multivalent ligands due to the resulting bivalency of dimeric fusion proteins, (2) longer serum half-life, (3) the ability to activate effector cells via the Fc domain, (4) ease of purification (for example, by protein A chromatography), (5) affinity for TNF-α or TNF-β cytotoxicity.

While this generally permits secretion of the fusion protein in the absence of an Ig light chain, a major embodiment of the present invention provides for the inclusion of the $CH_1$ domain, which can confer advantages such as (I) increased distance and/or flexibility between two receptor molecules resulting in greater affinity for TNF, (2) the ability to create a heavy chain fusion protein and a light chain fusion protein that would assemble with each other and dimerize to form a tetravalent (double fusion) receptor molecule, and (3) a tetravalent fusion protein can have increased affinity and/or neutralizing capability for TNF compared to a bivalent (single fusion) molecule.

Anti-Idiotype ABS

In addition to monoclonal or chimeric anti-TNF antibodies, the present invention is also directed to an anti-idiotypic (anti-Id) antibody specific for the anti-TNF antibody of the invention. An anti-Id antibody is an antibody which recognizes unique determinants generally associated with the antigen-binding region of another antibody. The antibody specific for TNF is termed the idiotypic or Id antibody. The anti-Id can be prepared by immunizing an animal of the same species and genetic type (e.g. mouse strain) as the source of the Id antibody with the Id antibody or the antigen-binding region thereof. The immunized animal will recognize and respond to the idiotypic determinants of the immunizing antibody and produce an anti-Id antibody. The anti-Id antibody can also be used as an "immunogen" to induce an immune response in yet another animal, producing a so-called anti-anti-Id antibody. The anti-anti-Id can be epitopically identical to the original antibody which induced the anti-Id. Thus, by using antibodies to the idiotypic determinants of a mAb, it is possible to identify other clones expressing antibodies of identical specificity. See for example, U.S. Pat. No. 4,699,880, which is herein incorporated by reference in its entirety.

An anti-idiotypic (anti-Id) antibody is an antibody which recognizes unique determinants generally associated with the antigen-binding site of an antibody. An anti-Id antibody can be prepared by immunizing an animal of the same species and genetic type (e.g., mouse strain) as the source of the mAb with the mAb to which an anti-Id is being prepared. The immunized animal will recognize and respond to the idiotypic determinants of the immunizing antibody by producing an antibody to these idiotypic determinants (the anti-Id antibody).

Accordingly, mAbs generated against TNF according to the present invention can be used to induce anti-Id antibodies in suitable animals, such as BALB/c mice. Spleen cells from such immunized mice can be used to produce anti-Id hybridomas secreting anti-Id mAbs. Further, the anti-Id mAbs can be coupled to a carrier such as keyhole limit hemocyanin (KLH) and used to immunize additional BALB/c mice. Sera from these mice will contain anti-anti-Id antibodies that have the binding properties of the original mAb specific for a TNF epitope.

Accordingly, any suitable TNF neutralizing compound can be used in methods according to the present invention. Examples of such TNF neutralizing compound can be selected from the group consisting of antibodies or portions thereof specific to neutralizing epitopes of TNF, p55 receptors, p75 receptors, or complexes thereof, portions of TNF receptors which bind TNF, peptides which bind TNF, may peptido mimetic drugs which bind TNF and any organo mimetic drugs that block TNF.

Such TNF neutralizing compounds can be determined by routine experimentation based on the teachings and guidance presented herein, by those skilled in the relevant arts.

Structural Analogs of Anti-TNF Antibodies and Anti-TNF Peptides

Structural analogs of anti-TNF Abs (including fragments and regions thereof), and antigens (also referred to herein as "peptides") that generate said Abs, of the present invention are provided by known method steps based on the teaching and guidance presented herein.

Knowledge of the three-dimensional structures of proteins is crucial in understanding how they function. The three-dimensional structures of more than 400 proteins are currently available in protein structure databases (in contrast to around 15,000 known protein sequences in sequence databases). Analysis of these structures shows that they fall into recognizable classes of motifs. It is thus possible to model a three-dimensional structure of a protein based on the proteins homology to a related protein of known structure. Many examples are known where two proteins that have relatively low sequence homology, can have very similar three dimensional structures or motifs.

In recent years it has become possible to determine the three dimensional structures of proteins of up to about 15 kDa by nuclear magnetic resonance (NMR). The technique only requires a concentrated solution of pure protein. No crystals or isomorphous derivatives are needed. The structures of a number proteins have been determined by this method. The details of NMR structure determination are well-known in the art. (See, e.g., Wuthrich., *NMR of Proteins and Nucleic Acids*, Wiley, New York, 1986; Wuthrich, K. *Science* 243:45-50 (1989); Clore et al. *Crit, Rev. Bioch, Molec. Biol.* 24:479-564 (1989); Cooke et al, *Bioassays* 8:52-56 (1988)).

In applying this approach, a variety of $^1$H NMR 2D data sets are collected for anti-TNF Abs and/or anti-TNF peptides of the present invention. These are of two main types. One type, COSY (Conetated Spectroscopy) identifies proton resonances that are linked by chemical bonds. These spectra provide information on protons that are linked by three or less covalent bonds. NOESY (nuclear Overhauser enhancement spectroscopy) identifies protons which are close in space (less than 0.5 nm). Following assignment of the complete spin system, the secondary structure is defined by NOESY. Cross peaks (nuclear Overhauser effects or NOE's) are found between residues that are adjacent in the primary sequence of the peptide and can be seen for protons less than 0.5 nm apart. The data gathered from sequential NOE's combined with amide proton coupling constants and NOE's from non-adjacent amino acids, that are adjacent to the secondary structure, are used to characterize the secondary structure of the polypeptides. Aside from predicting secondary structure, NOE's indicate the distance that protons are in space in both the primary amino acid sequence and the secondary structures. Tertiary structure predictions are determined, after all the data are considered, by a "best fit" extrapolation.

Types of amino acids are first identified using through-bond connectivities. The second step is to assign specific amino acids using through-space connectivities to neighboring residues, together with the known amino acid sequence. Structural information is then tabulated and is of three main kinds: The NOE identifies pairs of protons which are close in space, coupling constants give information on dihedral angles and slowly exchanging amide protons give information on the position of hydrogen bonds. The restraints are used to compute the structure using a distance geometry type of calculation followed by refinement using restrained molecular dynamics. The output of these computer programs is a family of structures which are compatible with the experimental data (i.e. the set of pairwise <0.5 nm distance restraints). The better that the structure is defined by the data, the better the family of structures can be superimposed, (i.e., the better the resolution of the structure). In the better defined structures using NMR, the position of much of backbone (i.e. the amide, C-α and carbonyl atoms) and the side chains of those amino acids that lie buried in the core of the molecule can be defined as clearly as in structures obtained by crystallography. The side chains of amino acid residues exposed on the surface are frequently less well defined, however. This probably reflects the fact that these surface residues are more mobile and can have no fixed position. (In a crystal structure this might be seen as diffuse electron density).

Thus, according to the present invention, use of NMR spectroscopic data is combined with computer modeling to arrive structural analogs of at least portions of anti-TNF Abs and peptides based on a structural understanding of the topography. Using this information, one of ordinary skill in the art will know how to achieve structural analogs of antiTNF Abs and/or peptides, such as by rationally-based amino acid substitutions allowing the production of peptides in which the TNF binding affinity is modulated in accordance with the requirements of the expected therapeutic or diagnostic use of the molecule, preferably, the achievement of greater specificity for TNF binding.

Alternatively, compounds having the structural and chemical features suitable as anti-TNF therapeutics and diagnostics provide structural analogs with selective TNF affinity. Molecular modeling studies of TNF binding compounds, such as TNF receptors, anti-TNF antibodies, or other TNF binding molecules, using a program such as MACROMODEL (Strödinger LLC), INSIGHT (Accelrys Inc.), and DISCOVER (Accelrys Inc.) provide such spatial requirements and orientation of the anti-TNF Abs and/or peptides according to the present invention. Such structural analogs of the present invention thus provide selective qualitative and quantitative anti-TNF activity in vitro, in situ and/or in vivo.

Anti-Viral Compounds

In a further embodiment, the compositions of the present invention comprise an anti-viral compound. Preferably, the anti-viral compound is an anti-coronaviral compound. The anti-coronaviral compound is preferably an antibody (e.g., monoclonal, polyclonal, chimeric, etc.), an inhibitor of viral RNA-dependent RNA polymerase, an inhibitor of a virus-encoded protease that affects processing of a viral RNA-dependent RNA polymerase, an inhibitor of coronavirus budding or release from infected cells, inhibitor of coronavirus budding or release from infected cells, such as one that affects the activity of hemagglutinin-esterase, an inhibitor of virus binding to a specific cell surface receptor (e.g., an inhibitor of the binding of hAPN to HCoV-229E), or an inhibitor of receptor-induced conformational changes in virus spike glycoprotein that are associated with virus entry and combinations thereof. More preferably, the anti-viral compound is a monoclonal antibody against a SARS-associated virus, such as SARS-CoV. According to an embodiment of the present invention, a monoclonal antibody of the present invention (having a half life of about 20 days) is administered to a subject as a prophylactic to SARS infection.

Anti-viral compounds include nucleoside/nucleotide reverse transcriptase inhibitors (NRTIs), non-nucleoside reverse transcriptase inhibitors (NNRTIs), and/or protease inhibitors (PIs) for example. NRTIs that may be administered in combination with the compositions of the invention, include, but are not limited to RETROVIR (Glaxo Smith Kline Inc., zidovudine/AZT), VIDEX (Bristol-Myers Squibb Inc.) didanosine/ddI), HIVID (Hoffmann-La Roche) (zalcitabine/ddC), ZERIT (Bristol-Myers Squibb, stavudine/d4T), EPIVIR (Glaxo Smith Kline, lamivudine/3TC), and COMBIVIR (Glaxo Smith Kline, zidovudine/lamivudine). NNRTIs that may be administered in combination with the compositions of the invention, include, but are not limited to, VIRAMUNE (Boehringer Ingelheim Pharmaceuticals Inc., nevirapine), RESCRIPTOR (Pharmacia/Upjohn, delavirdine), and SUSTIVA (Dupont Pharma Co., efavirenz). Protease inhibitors that may be administered in combination with the compositions of the invention, include, but are not limited to, CRIXIVAN (Merck & Co., indinavir), NORVIR (Abbott Labs., ritonavir), INVASE (Hoffmann-La Roche, saquinavir), and VIRACEPT (Agouron Pharma Inc., nelfinavir). In a specific embodiment, antiretroviral agents, nucleoside reverse transcriptase inhibitors, non-nucleoside reverse transcriptase inhibitors, and/or protease inhibitors may be used in any combination with compositions of the invention to treat AIDS and/or to prevent or treat HIV infection.

NRTIs include LODENOSINE (F-ddA; an acid-stable adenosine NRTI, Triangle/Abbott); COVIRACIL (emtricitabine/FTC); structurally related to lamivudine (3TC) but with 3- to 10-fold greater activity in vitro, Triangle/Abbott); dOTC (BCH-10652, also structurally related to lamivudine but retains activity against a substantial proportion of tamivudine-resistant isolates; Biochem Pharma); Adefovir (refused approval for anti-HIV therapy by FDA; Gilead Sciences); PREVEON (Gilead Sciences Inc.) (Adefovir Dipivoxil, the active prodrug of adefovir; its active form is PMEA-pp); TENOFOVIR, (bis-POC PMPA, a PMPA prodrug; Gilead); DAPD/DXG (active metabolite of DAPD; Triangle/Abbott); DD4FC (related to 3TC, with activity against AZT/3TC-resistant virus); GW420867X (Glaxo Wellcome); ZIAGEN (abacavir/159U89: Glaxo Wellcome Inc.); CS-87 (3'-azido-2',3'-dideoxyuridine: WO 99/66936); and S-acyt-2-thioethyl (SATE)-bearing prodrug forms of β-L-FD4C and β-L-FddC (WO 98/17281).

Other NNRTIs include COACTINON (Emivirine/MKC-442, potent NNRTI of the HEPT class; Triangle/Abbott); CAPRAVIRINE, (AG-1549/S-1153, a next generation NNRTI with activity against viruses containing the K103N mutation; Agouron); PNU-142721 (has 20- to 50-fold greater activity than its predecessor delavirdine and is active against K103N mutants; Pharmacia & Upjohn); DPC-961 and DPC-963 (second-generation derivatives of efavirenz, designed to be active against viruses with the K103N mutation; DuPont); GW-420867X (has 25-fold greater activity than HBY097 and is active against K103N mutants: Glaxo Wellcome); CALANOLIDE A (naturally occurring agent from the latex tree; active against viruses containing either or both the Y11C and K103N mutations); and Propolis (WO 99/49830).

Additional protease inhibitors include LOPINAVIR (ABT378/r; (Abbott Laboratories); BMS-232632 (an azapeptide; Bristol-Myers Squibb); TIPRANAVIR (PNU-140690, a non-peptidic dihydropyrone; Pharmacia & Upjohn); PD-178390 (a nonpeptidic dihydropyrone; Parke-Davis); BMS 232-632 (an azapeptide; Bristol-Myers Squibb); L-756,423 (an indinavir analog; Merck); DMP450 (a cyclic urea compound; Avid & DuPont 7: AG-1776 (a peptidomimetic with in vitro activity against protease inhibitor-resistant viruses; Agouron); VX-1751GW433908 (phosphate prodrug of amprenavir; Vertex & Glaxo Welcome); CGP61755 (Ciba); and AGENERASE (amprenavir, Glaxo Wellcome Inc,).

Additional antiretroviral agents include fusion inhibitors/gp41 binders, Fusion inhibitor g/gp41 binders include T-20 t a peptide from residues 643-678 of the HIV gp41 transmembrane protein ectodomain which binds to gp41 in its resting state and prevents transformation to the fusogenic state: Trimeris) and T-1249 (a second-generation fusion inhibitor; Trimeris).

Additional antiretroviral agents include fusion inhibitors/chemokine receptor antagonists. Fusion inhibitors/chemokine receptor antagonists include CXCR4 antagonists such as AMD 3100 (a bicyclam), SDF-1 and its analogs, and ALX404C (a cationic peptide), T22 (an. 18 amino acid peptide; Trimeris) and the T22 analogs T134 and T140; CCR5 antagonists such as RANTES (9-68), AOP-RANTES, NNY-RANTES, and TAK-779; and CCR5/CXCR4 antagonists such as NSC 651016 (adistamycin analog). Further included is FUZEON (generic name eufuvirtide; available from Hoffmann-La Roche; which blocks the ability of HIV to infect healthy CD4 cells). Also included are CCR2B, CCR3, and CCR6 antagonists. Chemokine receptor agonists such as RANTES, SDF-1, MIP-1α, MIP-1 β, etc., may also inhibit fusion.

Additional antiretroviral agents include integrase inhibitors. Integrase inhibitors include dicaffeoylquinic (DFQA) acids: L-chicoric acid (a dieaffeoyltartaric (DCTA) acid); quinalizarin (QLC) and related anthraquinones; ZINTEVIR (Aronex Pharmaceuticals Inc.) (AR 177, an oligonucleotide that probably acts at cell surface rather than being a true integrase inhibitor: Arondex); and naphthols such as those disclosed in WO 98/50347.

Additional antiretroviral agents include hydroxyurea-like compounds such as BCX-34 (Biocryst Pharma. Inc., a purine nucleoside phosphorylase inhibitor); ribonucleotide reductase inhibitors such as DIDOX (Molecules for Health Inc.): inosine monophosphate dehydrogenase (IMPDH) inhibitors such as VX497 (Vertex Pharmaceutical Inc.); and mycopholic acids such as CellCept (Hoffmann-La Roche, mycophenolate mofetil).

Other antiretroviral agents include inhibitors of viral integrase, inhibitors of viral genome nuclear translocation such as arylene bis(methylketone) compounds: inhibitors of HIV entry such as AOP-RANTES, NNY-RANTES, RANTES-IgG fusion protein, soluble complexes of RANTES and glycosaminoglycans (GAG), and AMD-3100 (AnorMed Inc.); nucleocapsid zinc finger inhibitors such as dithiane compounds: targets of HIV Tat and Rev; mid pharmacoenhancers such as ABT-378.

According to an embodiment, the compositions of the invention may comprise other antiretroviral compounds including cytokines and lymphokines such as MIP-1.α, MIP-1β, SDF-1.α, IL-2, PROLEUKIN (Chiron Corp.) (aldesleukin/L2-7001; Chiron), IL-4, IL-10. IL-12, and IL-13; inteferons such as IFN-β2a; antagonists of TNFs. NF.kappaB. GM-CSF, M-CSF, and IL-10; agents that modulate immune activation such as cyclosporin and prednisone; vaccines such as Remune (HIV Immunogen), recombinant gp120 and fragments, bivalent (B/E) recombinant envelope glycoprolein, rgp120CM235, MN rgp120, SF-2 rgp120, gp120/soluble CD4 complex, Delta JR-FL protein, branched synthetic peptide derived from discontinuous gp120 C3/C4 domain, fusion-competent immunogens, and Gag, Pol, Nef, and Tat vaccines; gene-based therapies such as genetic suppressor elements (GSEs; WO 98/54366), and intrakines (genetically modified CC chemokines targetted to the ER to block surface expression of newly synthesized CCR5 (Yang et al., PNAS 94:11567-72 (1997); Chen et al., Nat. Med. 3:111-16 (1997)); antibodies such as the anti-CXCR4 antibody 12G5, the anti-CCR5 antibodies 2D7, 5C7, PA8, PA9, PA10, PA11, PA12, and PA14. the anti-CD4 antibodies Q4120 and RPA-T4, the anti-CCR3 antibody 7B11, the anti-gp120 antibodies 17b, 48d, 447-52D, 257-D, 268-D and 50-1, anti-Tat antibodies, anti-TNF-α, antibodies, and monoclonal antibody 33A; aryl hydrocarbon (AH) receptor agonists and antagonists such as TCDD, 3,3',4,4',5-pentachlorobiphenyl, 3,3',4,4'-tetrachlorobiphenyl, and α-naphthoflavone (WO 98/30213); and anti-oxidants such as .gamma.-L-glutamyl-L-cysteine ethyl ester (γ-GCE; WO 99/56764).

In other embodiments, compositions of the invention additionally comprise anti-opportunistic infection agents. Anti-opportunistic agents include, but are not limited to, TRIMETHOPRIM-SULFAMETHOXAZOLE (Hoffmann-La Roche) DAPSON (Jacobus Pharmaceuticals), PENTAMIDINE (American Pharmaceuticals Partners), ATOVAQUONE (Glaxo SmithKline), ISONIAZID (Becton Dickinson Microbiology System), RIFAMPIN (Bedford Labs), PYRAZINAMIDE (Pharmascience Inc.), ETHAMBUTOL (Cadila Pharma Inc.), RIFABUTIN (Adria Labs Inc.), CLARITHROMYCIN (Ind-Swift Labs, Ltd), AZITHROMYCIN (Pfizer, Inc.), GANCICLOVIR, FOSCARNET (Astra Pharmaceuticals Inc.), CIDOFOVIR (Gilead Sciences Inc.), FLUCONAZOLE (Pfizer Inc.) ITRACONAZOLE (Jansseen Pharmaantica) KETOCONAZOLE (Novopharm Ltd.), ACYCLOVIR (Glaxo-Wellcome). FAMCICOLVIR, PYRIMETHAMINE (Glaxo Wellcome Inc.), LEUCOVORIN (Immunex/Amgen Inc.), NEUPOGEN (Amgen Inc.) (filgrastim/G-CSF), and LEUKINE (Berlex Labs Inc.) (sargramostim/GM-CSF).

According to an embodiment, the compositions of the invention comprise TRIMETHOPRIM-SULFAMETHO—XAZOLE (Hoffmann-La Roche), DAPSON (Jacobus Pharmaceuticals), PENTAMIDINE (American Pharmaceuticals Partners) and/or ATOVAQUONE (Glaxo SmithKline) to prophylactically treat or prevent an opportunistic *Pneumocystis carinii* pneumonia infection. In another specific embodiment, compositions of the invention are used in any combination with ISONIAZID (Becton Dickinson Microbiology System), RIFAMPIN (Bedford Labs), PYRAZINAMIDE (Pharmascience Inc.), and/or ETHAMBUTOL (Cadila Pharma Inc.) to prophylactically treat or prevent an opportunistic *Mycobacterium avium* complex infection. In another specific embodiment, compositions of the invention are used in any combination with RIFABUTIN (Adria Labs Inc.), CLARITHROMYCIN (Ind-Swift Labs, Ltd.), and/or AZIRTHROMYCIN (Pfizer Inc.) to prophylactically treat or prevent an opportunistic *Mycobacterium tuberculosis* infection. In another specific embodiment, compositions of the invention are used in any combination with GANCICLOVIR, FOSCARNET (Astra Pharmaceuticals Inc.), and/or CIDOFOVIR (Gillhead Sciences Inc.) to prophylactically treat or prevent an opportunistic cytomegalovirus infection. In another specific embodiment, compositions of the invention are used in any combination with FLUCONAZOLE (Pfizer Inc.), ITRACONAZOLE (Janssen Pharmaantica), and/or KETOCONAZOLE (Novopharm Ltd.) to prophylactically treat or prevent an opportunistic fungal infection. In another specific embodiment, compositions of the invention are used in any combination with ACYCLOVIR (Glaxo-Wellcome) and/or FAMCICOLVIR to prophylactically treat or prevent an opportunistic herpes simplex virus type I and/or type II infection. In another specific embodiment, compositions of the invention are used in any combination with PYRIMETHAMNE and/or LEUCOVORIN (Immunex/Amgen Inc.) to prophylactically treat or prevent an opportunistic *Toxoplasma gondii* infection. In another specific embodiment, compositions of the invention are used in any combination with LEUCOVORIN (Immunex/Amgen Inc.) and/or NEUPOGEN (Amgen Inc.) to prophylactically treat or prevent an opportunistic bacterial infection.

In a further embodiment, compositions of the invention comprise an antibiotic agent. Antibiotic agents that may be administered include, but are not limited to, amoxicillin, β-lactainases, aminoglycosides, betalactam (glycopeptide), βlactamases, Clindamycin, chloramphenicol, cephalosporins, ciprofloxacin, erythromycin, fluoroquinolones, macrolides, metronidazole, penicillins, quinolones, rapamycin, rifampin, streptomycin, sultonamide, tetracyclines, trimtethoprim, trimethoprim-sulfamethoxazole, and vancomycin.

According to an implementation, the compositions of the invention comprise immunestimulants. Immunostimulants that may be administered in combination with the Therapemics of the invention include, but are not limited to, levamisole (e.g., ERGAMISOL), isoprinosine (e.g. OSIPLEX), interferons (e.g., interferon α), and interleukins (e.g., IL-2).

According to an implementation, the compositions of the invention comprise immunosuppressive agents. Immunosuppressive agents that may be administered in combination with the compositions of the invention include, but are not limited to, steroids, cyclosporine, cyclosporine analogs, cyclophosphamide methylprednisone, prednisone, azathioprine, FK-506, 15-deoxyspergualin, and other immunosuppressive agents that act by suppressing the function of responding T cells. Other immunosuppressive agents that may be administered in combination with the compositions of the invention include, but are not limited to, prednisolone, methotrexate, thalidomide, methoxsalen, rapamycin, leflunomide, mizoribine (BREDNIN) (Boehringer-Ingelheim Inc.), brequinar, deoxyspergualin, and azaspirane (SKF 105685), ORTHOCLONE OKT (OrthoBiotech Products L.P.) 3 (muromonab-CD3), SANDIMMUNE, NEORAL (Novartis Inc.), SANGDYA (Sangstat Medical Corp.) cyclosporine), PROGRAF (Fujisawa Healthcare Inc.) (FK506, tacrolimus), CELLCEPT (Hoffmann-La Roche) (mycophenolate motefil, of which the active metabolite is mycophenolic acid), IMURAN (Glaxo SmithKline) (azathioprine), glucocorticosteroids, adrenocortical steroids such as DELTASONE (UpJohn/Pharmacia) (prednisone) and HYDELTRASOL (DuPont, Merck & Co. Inc.) (prednisolone), FOLEX (Adria Laboratories, Inc.) and MEXATE (Lederle Laboratories Inc.) methotrxate), OXSORALEN-ULTRA (ICN Pharmaceuticals, Inc.) (methoxsalen) and RAPAMUNE (Wyeth Inc.) (sirolimus). In a specific embodiment, immunosuppressants may be used to prevent rejection of organ or bone marrow transplantation.

According to an implementation, the compositions of the invention comprise intravenous immune globulin preparations. Intravenous immune globulin preparations that may be administered include, but are not limited to, GAMMAR, IVEEGAM (Baxter Inc.), SANDOGLOBULIN (Novartis, Inc.) GAMMAGARD (Baxter Corp.) S/D, ATGAM (Pharmacia/Upjohn/Pfizer), (antithymocyte glubulin), and GAMIMUNE (Bayer Inc.). In a specific embodiment, compositions of the invention are administered in combination with intravenous immune globulin preparations in transplantation therapy (e.g., bone marrow transplant).

In certain embodiments, the compositions of the invention comprise an anti-inflammatory agent. Anti-inflammatory agents that may be administered include, but are not limited to, corticosteroids (e.g. βmethasone, budesonide, cortisone, dexamethasone, hydrocortisone, methylprednisolone, prednisolone, prednisone, and triamcinolone), nonsteroidal anti-inflammatory drugs (e.g., diclofenac, diflunisal, etodolac, fenoprofen, floctafenine, flurbiprofen, ibuprofen, indomethacin, ketoprofen, meclofenamate, mefenamic acid, meloxicam, nabumetone, naproxen, oxaprozin, phenylbutazone, piroxicam, sulindac, tenoxicam, tiaprofenic acid, and tolmetin.), as well as antihistamines, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

Immune Globulins

Hyperimmune CMV immunoglobulin has attenuated CMV disease associated with kidney transplantation, but it has not proved useful in preventing CMV disease in HIV-infected persons. A human monoclonal anticytomegalovirus antibody may be useful as adjunctive therapy with foscamet or ganciclovir for treatment of CMV retinitis.

Interferons

Interferons are natural cellular products released from infected host cells in response to viral or other foreign nucleic acids. They are detectable as early as 2 h after infection. Their complex mechanism of action has not been fully established, but interferon selectively blocks translation and transcription of viral RNA stopping viral replication without disturbing normal host cell function.

A recombinant form of endogenous interferon-α is being studied in selected patients with hairy cell leukemia, Kaposi's sarcoma, human papillomavirus, and respiratory viruses. It is used primarily for hepatitis B and C. Patients with active HBV or hepatitis C virus (HCV) with detectable viral loads and abnormal liver function tests may benefit from therapy.

In patients with HBV who fit appropriate criteria, 2.5 to 5 million U sc or IM for 4 to 6 mo can induce clearance of HBV DNA and the hepatitis B e antigen (HBeAg) from serum and improve liver function test abnormalities and liver histology in 25 to 40% of patients. For chronic delta hepatitis, higher doses in the range of 9 to 10 million U 3 times/wk are required, and relapse is very common. For HCV, 3 to 6 mo of 3 to 6 million U 3 times/wk for 6 to 12 mo typically decreases HCV RNA level mid improves liver function tests and liver histology in 10 to 25%. Adverse effects include fever, chills, weakness, and myalgia typically starting 7 to 12 h after first injection and lasting up to 12 h. The lower dose used in HCV leads to less severe adverse effects although worsening of hepatitis has been reported, Addition of ribavirin to interferon for HCV shows promise.

Therapeutic Administration

The subject methods involve administering to the patient the compositions of the invention. According to an embodiment of the invention SARS-associated inflammatory cytokine inhibitor is administered to a SARS patient. According to a further embodiment, a TNF inhibitor is administered to a SARS patient. Anti-TNF recombinant receptors, mAbs, antisense oligonucleotides, peptides, fragments and derivatives thereof, and small molecules of the present invention, as described herein, can be administered either as individual therapeutic agents or in combination with other therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.01 to 100 milligrams per kilogram of body weight. Ordinarily 1.0 to 5, and preferably 1 to 10 milligrams per kilogram per day given in divided doses 1 to 6 times a day or in sustained release form is effective to obtain desired results.

As a non-limiting example, treatment of SARS can be provided as a daily dosage of anti-TNF peptides, monoclonat chimeric and/or routine antibodies of the present invention O. 1 to 100 mg/kg, such as 0.5, 0.9, 1.0, 1.1, 1.5, 2, 3, 4.5, 6, 7.8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7.8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of week 1, 2, 3, 4, 5, 6, 7, 8, 9, 10, 11, 12, 13, 14, 15, 16, 17, 18, 19 or 20, or any combination thereof, using single or divided doses of every 24, 12, 8, 6, 4 or 2 hours, or any combination thereof.

Since circulating concentrations of TNF tend to be extremely low, in the range of about 10 pg/ml in non-septic individuals, and reaching about 50 pg/ml in septic patients and above 100 pg/ml in the sepsis syndrome (Hammerle, A. F. et al, 1989, infra) or can only be detectable at sites of TNF-mediated pathology, it is preferred to use high affinity and/or potent in vivo TNF-inhibiting and/or neutralizing antibodies, fragments or regions thereof, for both TNF immunoassays and therapy of TNF-mediated pathology. Such antibodies, fragments, or regions, will preferably have an affinity for hTNF-α, expressed as Ka, of at least $10^8$ $M^{-1}$, more preferably, at least $10^9$ $M^{-1}$, such as $10^8$-$10^{10}$ $M^{-1}$, $5 \times 10^8$ $M^{-1}$, $8 \times 10^8$ $M^{-1}$, $2 \times 10^9$ $M^{-1}$, $4 \times 10^9$ $M^{-1}$, $6 \times 10^9$ $M^{-1}$, $8 \times 10^9$ $M^{-1}$, or any range or value therein.

Preferred for human therapeutic use are high affinity murine and chimeric antibodies, and fragments, regions and derivatives having potent in vivo TNF-α-inhibiting and/or neutralizing activity, according to the present invention, that block TNF-induced IL-6 secretion. Also preferred for human therapeutic uses are such high affinity murine and chimeric anti-TNF-α antibodies, and fragments, regions and derivatives thereof, that block TNF-induced procoagulant activity, including blocking of TNF-induced expression of cell adhesion molecules such as ELAM-I and ICAM-1 and blocking of TNF mitogenic activity, in vivo. in situ, and in vitro.

The compositions of the present invention preferably include a pharmaceutically acceptable carrier. Suitable pharmaceutically acceptable carriers and/or diluents include any and all conventional solvents, dispersion media, fillers, solid carriers, aqueous solutions, coatings, antibacterial and antifungal agents, isotonic and absorption delaying agents, and the like. Suitable pharmaceutically acceptable carriers include, for example, one or more of water, saline, phosphate buffered saline, dextrose, glycerol, ethanol and the like, as well as combinations thereof. Pharmaceutically acceptable carriers may further comprise minor amounts of auxiliary substances such as wetting or emulsifying agents, preservatives or buffers, which enhance the shelf life or effectiveness of the composition. The preparation and use of pharmaceutically acceptable carriers is well known in the art. Except insofar as any conventional media or agent is incompatible with the active ingredient, use thereof in the compositions of the present invention is contemplated.

The present compositions can be administered by any conventional route, including parenterally, e.g., by injection, either subcutaneously or intramuscularly, for example, as well as orally or intranasally. Methods for intramuscular injection are described by Wolff et al. and by Sedegah et al. Other modes of administration employ oral formulations, pulmonary formulations, suppositories, and transdermal applications, for example, without limitation. Oral formulations, for example, include such normally employed excipients as, for example, pharmaceutical grades of mannitol, lactose, starch, magnesium stearate, sodium saccharine, cellulose, magnesium, carbonate, and the like, without limitation.

Dosage forms (compositions) suitable for internal administration generally contain from about 0.1 milligram to about 500 milligrams of active ingredient per unit. In these pharmaceutical compositions the active ingredient will ordinarily be present in an amount of about 0.5-95% by weight based on the total weight of the composition.

For parenteral administration, anti-TNF peptides or antibodies can be formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and nonaqueous vehicles such as fixed oils can also be used. The vehicle or lyophilized powder can contain additives that maintain isotonicity (e.g., sodium chloride, mannitol) and chemical stability (e.g., buffers and preservatives). The formulation is sterilized by commonly used techniques.

Suitable pharmaceutical carriers are described in the most recent edition of Remington's Pharmaceutical Sciences, A. Osol, a standard reference text in this field of art. The compositions and methods of the present invention may be used in combination with other therapies, such as supportive therapy, for example, in accordance with an implementation of the present invention.

According to an implementation of the present invention, a composition of the invention may be administered to a patient along with intravenous (IV) fluids. For example, the present compositions may be contained within the intravenous (IV) bag or may be injected into the lock of intravenous (IV) line.

In another implementation, the composition of the present invention may be administered to a patient along with oxygen or other such treatment. For example, a composition of the invention may be administered via a nebulizer.

For example, a parenteral composition suitable for administration by injection is prepared by dissolving 1.5% by weight of active ingredient in 0.9% sodium chloride solution.

Any efficacious route of administration may be used to therapeutically administer the TNF inhibitors. If injected, the inhibitors can be administered, for example, via intra-articular, intravenous, intramuscular, intralesional, intraperitoneal or subcutaneous routes by bolus injection or by continuous infusion. Other suitable means of administration include sustained release from implants, aerosol inhalation, eyedrops, oral preparations, including pills, syrups, lozenges or chewing gum, and topical preparations such as lotions, gels, sprays, ointments or other suitable techniques. Alternatively, proteinaceous TNF inhibitors, such as a soluble TNFR, may be administered by implanting cultured cells that express the protein. When the inhibitor is administered in combination with one or more other biologically active compounds, these may be administered by the same or by different routes, and may be administered simultaneously, separately or sequentially.

TNFR:Fc or other soluble TNFRs or other TNF inhibitors preferably are administered in the form of a physiologically acceptable composition comprising purified recombinant protein in conjunction with physiologically acceptable carriers, excipients or diluents. Such carriers are nontoxic to recipients at the dosages and concentrations employed. Ordinarily, the preparation of such compositions entails combining the TNF-α antagonist with buffers, antioxidants such as ascorbic acid, low molecular weight polypeptides (such as those having fewer than 10 amino acids), proteins, amino acids, carbohydrates such as glucose, sucrose or dextrins, chelating agents such as EDTA, glutathione and other stabilizers and excipients. Neutral buffered saline or saline mixed with conspecific serum albumin are exemplary appropriate diluents. In accordance with appropriate industry standards, preservatives may also be added, such as benzyl alcohol. TNFR:Fc preferably is formulated as a lyophilizate using appropriate excipient solutions (e.g., sucrose) as diluents. Suitable components are nontoxic to recipients at the dosages and concentrations employed. Further examples of components that may be employed in pharmaceutical formulations are presented in Remington's Pharmaceutical Sciences, $16^{th}$ Ed., Mack Publishing Company, Easton, Pa., 1980.

Appropriate dosages can be determined in standard dosing trials, and may vary according to the chosen route of administration. The amount and frequency of administration will depend on such factors as the nature and severity of the indication being treated, the desired response, the age and condition of the patient, and so forth.

In one embodiment of the invention, TNFR:Fc is administered one time per week to treat the various medical disorders disclosed herein, in another embodiment is administered at least two times per week, and in another embodiment is administered at: least three times per week. An adult patient is a person who is 18 years of age or older. If injected, the effective amount of TNFR:Fc per adult dose ranges from 1-20 mgm$^2$, and preferably is about 5-12 mg/m$^2$. Alternatively, a flat dose may be administered, whose amount may range from 5-100 mg/dose. Exemplary dose ranges for a flat dose to be administered by subcutaneous injection are 5-25 mg/dose, 25-50 mg/dose and 50-100 mg/dose. In one embodiment of the invention, the various indications described below are treated by administering a preparation acceptable for injection containing TNFR:Fc at 25 mg/dose, or alternatively, containing 50 mg per dose. The 25 mg or 50 mg dose may be administered repeatedly. If a route of administration other than injection is used, the dose is appropriately adjusted in accord with standard medical practices. In many instances, an improvement in a patient's condition will be obtained by injecting a dose of about 25 mg of TNFR:Fc one to three times per week over a period of at least three weeks, or a dose of 50 mg of TNFR:Fc one or two times per week for at least three weeks, though treatment for longer periods may be necessary to induce the desired degree of improvement.

For pediatric patients (age 4-17), any suitable regimen may be used. Preferably, the regimen involves the subcutaneous injection of 0.4 mg/kg, up to a maximum dose of 25 mg of TNFR:Fc, administered by subcutaneous injection one or more times per week.

The invention further includes the administration of a soluble TNFR, such as TNFR:Fc, concurrently with one or more other drugs that are administered to the same patient in combination with the soluble TNFR, each drug being administered according to a regimen suitable for that medicament. "Concurrent administration" encompasses simultaneous or sequential treatment with the components of the combination, as well as regimens in which the drugs are alternated, or wherein one component is administered long-term and the other(s) are administered intermittently. Components may be administered in the same or in separate compositions, and by the same or different routes of administration. Examples of drugs to be administered concurrently include but are not limited to antivirals, antibiotics, analgesics, corticosteroids, antagonists of inflammatory cytokines, DMARDs and non-steroidal anti-inflammatories. DMARDs that can be administered in combination with the subject TNF-α inhibitors such as TNFR:Fc include azathioprine, cyclophosphamide, cyclosporine, hydroxychloroquine sulfate, methotrexate, leflunomide, minocycline, penicillamine, sulfasalazine and gold compounds such as oral gold, gold sodium thiomalate and aurothioglucose. Additionally, TNFR:Fc may be combined with a second TNF-α antagonist, including an antibody against TNF-α or TNFR, a TNF-α derived peptide that acts as a competitive inhibitor of TNF-α (such as those described in U.S. Pat. No. 5,795,859 or U.S. Pat. No. 6,107,273), a TNFR-IgG fusion protein other than etanercept, such as one containing the extracellular portion of the p55 TNF-α receptor, a soluble TNFR other than an IgG fusion protein, or other molecules that reduce endogenous TNF-α levels such as inhibitors of the TNF-α converting enzyme (see e.g., U.S. Pat. No. 5,594,106), or any of the small molecules or TNF-α inhibitors that are described above, including pentoxifylline or thalidomide.

If an antibody against TNF-α is used as the TNF-α inhibitor, a preferred dose range is 0.1 to 20 mg/kg, and more preferably is 1-10 mg/kg. Another preferred dose range for anti-TNF-TNF-α, antibody is 0.75 to 7.5 mg/kg of body weight. Humanized antibodies are preferred, that is, antibodies in which only the antigen-binding portion of the antibody molecule is derived from a non-human source. An exemplary humanized antibody for treating the hereindescribed diseases is infliximab (sold by Centocor as REMICADE (Centocor Inc.), which is a chimeric IgG1.kappa. monoclonal antibody having an approximate molecular weight of 149,100 daltons, Infliximab is composed of human constant and murine variable regions, and binds specifically to human TNF-α Other suitable anti-TNF-α, antibodies include the humanized antibodies D2E7 and CDP571, and the antibodies described in EP 0 516 785 B1. U.S. Pat. No. 5,656,272, EP 0 492 448 A1. Such antibodies may be injected or administered intravenously.

In one preferred embodiment of the invention, the various medical disorders disclosed herein as being treatable with inhibitors of TNF-α are treated in combination with another cytokine or cytokine inhibitor. For example, a soluble TNFR such as TNFR:Fc may be administered in a composition that also contains a compound that inhibits the interaction of other inflammatory cytokines with their receptors. Examples of cytokine inhibitors used in combination with TNFR:Fc include, for example, antagonists of TGF-β, II-6 or II-8.

TNF-α inhibitors such as TNFR:Fc also may be administered in combination with the cytokines GM-CSF, IL2 and inhibitors of protein kinase A type I to enhance T cell proliferation in HIV-infected patients who are receiving anti-retroviral therapy. In addition, TNF-α inhibitors may be combined with inhibitors of IL-13 to treat Hodgkin's disease.

Other combinations for treating the hereindescribed diseases include TNFR:Fc administered concurrently with compounds that are antivirals.

In addition, the subject invention provides methods for treating a human patient in need thereof, the method involving administering to the patient a therapeutically effective amount of a TNF-α inhibitor and an IL-6 inhibitor.

The present invention also relates to the use of the disclosed TNF-α inhibitors, such as TNFR:Fc. in the manufacture of a medicament for the prevention or therapeutic treatment of SARS.

The present invention also provides anti-TNF compounds and compositions comprising anti-TNF antibodies (Abs) and/or anti-TNF peptides which inhibit and/or neutralize TNF biological activity in vitro, in situ and/or in vivo, as specific for association with neutralizing epitopes of human tumor necrosis factor α (hTNF, α) and/or human tumor necrosis factor β (hTNF, β). Such anti-TNF Abs or peptides have utilities for use in treating SARS.

Anti-TNF compounds and compositions of this invention can be adapted for therapeutic efficacy by virtue of their ability to mediate antibody-dependent cellular cytotoxicity (ADCC) and/or complement-dependent cytotoxicity (CDC) against cells having TNF associated with their surface. For these activities, either an endogenous source or an exogenous source of effector cells (for ADCC) or complement components (for CDC) can be utilized. The murine and chimeric antibodies, fragments and regions of this invention, their fragments, and derivatives can be used therapeutically as immunoconjugates (see for review: Dillman, R. O., Ann. Int. Med. 111:592-603 (1989)). Peptides or Abs can be coupled to cytotoxic proteins, including, but not limited to ricin-A, Pseudomonas toxin and Diphtheria toxin. Toxins conjugated to antibodies or other ligands or peptides are well known in the art (see, for example, Olsnes, S. et al., Immunol. Today 10:291-295 (1989)). Plant and bacterial toxins typically kill cells by disrupting the protein synthetic machinery.

Anti-TNF compounds and compositions of this invention can be conjugated to additional types of therapeutic moieties including, but not limited to, radionuclides, therapeutic agents, cytotoxic agents and drugs. Examples of radionuclides which can be coupled to antibodies and delivered in vivo to sites of antigen include $^{212}$Bi, $^{132}$I, $^{186}$Re, and $^{90}$Y, which list is not intended to be exhaustive. The radionuclides exert their cytotoxic effect by locally irradiating the cells, leading to various intracellular lesions; as is known in the art of radiotherapy.

Cytotoxic drugs which can be conjugated to anti-TNF peptides and/or antibodies and subsequently used for in vivo therapy include, but are not limited to, daunorubicin, doxorubicin, methotrexate, and Mitomycin C. Cytotoxie drugs interfere with critical cellular processes including DNA, RNA, and protein synthesis. For a description of these classes of drugs which are well known in the art, and their mechanisms of action, see Goodman, et al., Goodman and Gilman's THE PHARMACOLOGICAL BASIS OF THERAPEUTICS, 8th Ed., Macmillan Publishing Co., 1990.

Anti-TNF compounds and compositions, such as the peptides and/or antibodies of this invention, can be advantageously utilized in combination with other monoclonal or routine mad chimeric antibodies, fragments and regions, or with lymphokines or hemopoietic growth factors etc., which serve to increase the number or activity of effector cells which interact with the antibodies.

Anti-TNF compounds and compositions, such as the peptides and/or antibodies, fragments or derivatives of this invention, can also be used in combination with TNF therapy to block undesired side effects of TNF. Recent approaches to cancer therapy have included direct administration of TN; to cancer patients or immunotherapy of cancel patients with lymphokine activated killer (LAK) cells (Rosenberg et al., New Eng. J. Med. 313:1485-1492 (1985)) or tumor infiltrating lymphocytes (TIL) (Kumick et al. (Clin. Immunol Immunopath. 38:367-380 (1986); Kradin et al., Cancer Immunol. Immunother. 24:76-85 (1987); Kradin et al., Transplant. Proc. 20:336-338 (1988)). Trials are currently underway using modified LAK cells or TIL which have been transfected with the TNF gene to produce large amounts of TNF. Such therapeutic approaches are likely to be associated with a number of undesired side effects caused by the pleiotropic actions of TNF as described herein and known in the related arts. According to the present invention, these side effects can be reduced by concurrent treatment of a subject receiving TNF or cells producing large amounts of TIL with the antibodies, fragments or derivatives of the present invention. Effective doses are as described above. The dose level will require adjustment according to the dose of TNF or TNF-producing cells administered, in order to block side effects without blocking the main anti-tumor effect of TNF. A person of ordinary skill in the art would know how to determine such doses without undue experimentation.

Screening Methods

The present invention contemplates screening methods for identifying a SARS-associated inflammatory cytokine inhibitor, In accordance with an implementation, a screening method comprises: administering a candidate SARS-associated inflammatory cytokine inhibitor to a group of patients infected by an infectious agent associated with SARS in a randomized placebo-controlled study; and monitoring the effectiveness of the candidate SARS-associated inflammatory cytokine inhibitor. Preferably, the candidate SARS-associated inflammatory cytokine inhibitor is a soluble recombinant SARS-associated inflammatory cytokine receptor, an antibody to a SARS associated inflammatory cytokine, a small molecule that affects the activity of a SARS-associated inflammatory cytokine, a SARS-associated antisense oligonucleotide or a combination thereof. A person of skill in the art would readily be able to routinely identify such a compound in this manner, based upon the guidance provided herein.

In accordance with another implementation of the present invention, a method of screening for a composition effective in treating a SARS patient comprises: administering a candidate TNF inhibitor to a group of patients infected by an infectious agent associated with SARS in a randomized placebo-controlled study; and monitoring the effectiveness of the candidate TNF inhibitor. Preferably, the candidate TNF inhibitor is a soluble recombinant TNF receptor, an antibody to TNF, a small molecule that affects the activity of a TNF, a TNF antisense oligonucleotide or a combination thereof. A person of skill in the art would readily be able to routinely identify a TNF inhibitor in such a manner, based upon the guidance provided herein.

In accordance with another implementation of the present invention, a method of screening for a composition effective in treating a SARS patient comprises: administering a candidate anti-viral compound to a group of patients infected by an infectious agent associated with SARS in a randomized placebo-controlled study: and monitoring the effectiveness of the candidate anti-viral compound. Preferably, the candidate anti-viral compound is a candidate anti-coronaviral compound. The candidate anti-coronaviral compound is preferably an antibody (e.g., monoclonal, polyclonal, chimeric, etc.) against a virus, an inhibitor of viral RNA-dependent RNA polymerase, an inhibitor of virus-encoded protease that affects processing of a infected cells, inhibitor of coronavirus budding or release from infected cells, such as one that affects the activity of hemagglutinin-esterase, an inhibitor of virus binding to a specific cell surface receptor (e.g., an inhibitor of the binding of hAPN to HcoV-229E, an inhibitor of receptor-induced conformational changes in virus spike glycoprotein that are associated with virus entry and combinations thereof. More preferably, the candidate anti-viral compound is a monoclonal antibody against a SARS-associated virus, such as SARS-CoV. A person of skill in the art would readily be able to routinely identify an anti-viral compound effective in treating SARS in such a manner, based upon the guidance provided herein.

The description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

A person skilled in the art would know, or be able to ascertain, using no more than routine experimentation, many equivalents to the specific embodiments of the invention described herein, based upon the guidance provided herein. The following examples are included to demonstrate preferred embodiments of the invention. It should be appreciated by those skilled in the art that the techniques disclosed in the examples which follow represent techniques discovered by the inventors to function well in the practice of the invention, and thus can be considered to constitute preferred modes for its practice. However, those of skill in the art should, in view of the present disclosure, appreciate that many changes can be made in the specific embodiments which are disclosed and still obtain a like or similar result without departing from the spirit and scope of the invention. The following examples are offered by way of illustration, and not by way of limitation.

EXAMPLES

Example I

In Vivo Efficacy of a Soluble Recombinant TNFR in Treating SARS

A soluble recombinant TNFR is tested in a randomized controlled study. Fifty adult patients (i.e. eighteen years of age or older) laboratory-confirmed as being infected by SARS-CoV are administered a single dose of either 1, 5, 12 or 20 mg/m$^2$TNFR:Fc. Another sixty patients will receive 100 milligrams of TNFR:Fc followed with either placebo or 1, 5, 12 or 20 milligrams TNFR:Fc. The TNFR:Fc is administered as a single injection. Clinical assessment, vital signs, and laboratory parameters are measured before, during and periodically for 28 days after the infusion.

Clinical Monitoring

Patients are monitored for 24 hours after infusions for hemodynamic change, fever or other adverse events. Clinical response studies are comprised of the following parameters:

Vital signs are recorded every 15 to 30 minutes during infusions, and at intervals following post infusion. A complete physical examination is performed at screening and conclusion of the treatment course. In addition, patients are monitored by standard laboratory tests including complete blood count, C3 and C4 components of complement, IgG, IgM and IgA, serum electrolytes, creatinine, urea, alkaline phosphatase, aspartate transaminase and total bilirubin. Urine analysis and culture is also be performed at each assessment point to determine levels of TNF and/or SARS-CoV present.

Response Assessment

The patients are assessed for response to the treatment at weeks 1, 2, 3, 4, 6 and 8 of the trial. The assessments are made between 0700 and 13 hours by the same observer. The following clinical assessments include: temperature, subjective feelings of respiratory distress, objective analysis of respiratory state (i.e., lung assessment), frequency of cough over a set period of time, radiological exam, and sera exam. In addition, the patients' global assessments of response are recorded on a 5-point scale (worse, no response, fair response, good response, excellent response). Sera positive by immunofluorescence is screened for antibodies.

Cytokine Assays

Bioactive TNF are measured in sera using the WEHI 164 clone 13 cytotoxicity assay (Espevik et al., J. Imm. Methods 95:99-105 (1986). Total IL-6 is measured in sera using a commercial immunoassay (Medgenix Diagnostics, SA, Belgium) and by a sandwich ELISA using monoclonal antibodies. Microtiter plates are coated with monoclonal antibody LNI 314-14 at a concentration of 3 ug/ml for 18 hours at 4° C. and blocked with 3% bovine serum albumin in 0.1M phosphate buffered saline, pH 7.2. Undiluted sera or standards (recombinant hIL 6, 0-8.1 ug/ml) are added to the wells in duplicate and incubated for 18 hours at 4° C. Bound IL-6 should be detected by incubation with monoclonal antibody LNI 110-14 after 90 minutes at 37° C. followed by biotin labeled goat anti-murine IgG2b for 90 minutes at 37° C. Southern Biotechnology, Birmingham, Ala.). The assay is developed using streptavidin-alkaline phosphatase (Southern Biotechnology) and p-nitrophenylphosphate as a substrate and the optical density read at 405 nm.

Disease Activity

The pattern of response for each of the clinical assessments of disease activity is assessed according to typical clinical assessment for SARS. Clinical assessments demonstrate improvement following the treatment. Respiratory distress decreases from a median of 2 days at entry to week 6. Similarly, the temperature and other flu like symptoms improve over the period of 24 hours to 3 weeks.

The response data is analyzed for each individual patient. Although the study is primarily designed to assess the short-term effects of TNF inhibitory treatment, follow-up clinical and laboratory data is made available for those patients followed for sufficient time. The duration of response in these patients is defined as the duration of a 20% (or greater) mean improvement in the selected activity measures. Comparison of the clinical and laboratory data for patients treated with infusions of TNFR:Fc (each at 10 m/kg) compared with those treated with 4 infusions (each at 5 mg/kg) is used to show differences in the rapidity or extent of response. In patients administered an appropriate dosage of the TNF inhibitor, at least about a 20% decrease in adult respiratory distress syndrome (ARDS) is observed, including each of chronic pulmonary function, diffusion capacity and lung compliance, with adequate patient tolerance. About a 20% decrease in mortality is also observed.

Immunological Investigations and Cytokines

Sera from the patients is also tested for the presence of bioactive TNF, using the WEHI 164 clone 13 cytotoxicity assay (Espevik et al., *J. Imm. Methods* 95:99-105 (1986)). Additionally, since production of CRP and SAA is thought to be regulated in large part by IL-6, serum levels of this cytokine are measured using 2 different assays, the Medgenix assay and an ELISA, which measure total IL-6.

Example II

In Vivo Efficacy of a Small Molecule Inhibitor for Treatment of SARS

In a placebo-controlled study, patients having SARS (infected with SARS-CoV-laboratory confirmed) are administered the following proposed treatments. Fifty patients with SARS-CoV are administered a single dose of either 100, 200, 300 or 400 milligrams of thalidomide. Another 60 patients receive 100 milligrams of thalidomide, and then either placebo or 100, 200, 300 or 400 milligrams thalidomide per kilogram bodyweight. The thalidomide is administered orally. Clinical assessment, vital signs, and laboratory parameters are measured before, during and periodically for 28 days after the infusion.

Clinical Monitoring

Patients are monitored during and for 24 hours after infusions for hemodynamic change, fever or other adverse events. Clinical response studies are comprised of the following parameters. Vital signs are recorded every 15 to 30 minutes during administration and at intervals following post administration. A complete physical examination is performed at screening and conclusion of the treatment course. In addition, patients are monitored by standard laboratory tests including complete blood count, C3 and C4 components of complement, IgG, IgM and IgA, serum electrolytes, creatinine, urea, alkaline phosphatase, aspartate transaminase and total bilirubin. Urine analysis and culture is also performed at each assessment point to determine levels of TNF and/or coronavirus present.

Response Assessment

The patients are assessed for response to the treatment at weeks 1, 2, 3, 4, 6 and 8 of the trial. The assessments are made between 0700 and 1300 hours by the same observer. The following clinical assessments made include: temperature, subjective feeling of respiratory distress, objective analysis of respiratory state (i.e. lung assessment) frequency of cough over a set period of time, radiological exam, and sera exam. In addition, the patients' global assessments of response are recorded on a 5-point scale (worse, no response, fair response, good response, excellent response). Sera positive by immunofluorescence is screened for antibodies.

Cytokine Assays

Bioactive TNF is measured in sera using the WEHI 164 clone 13 cytotoxicity assay (Espevik et al., *J. Imm. Methods* 95:99-105 (1986). Total IL-6 is measured in sera using a commercial immunoassay (Medgenix Diagnostics, SA, Belgium) and by a sandwich ELISA using monoclonal antibodies. Microtiter plates are coated with monoclonal antibody LNI 314-14 at a concentration of 3 ug/ml for 18 hours at 4° C. and blocked with 3% bovine serum albumin in 0.1M phosphate buffered saline, pH 7.2. Undiluted sera or standards (recombinant hIL 6, 0-8.1 ug/ml) are added to the wells in duplicate and incubated for 18 hours at 4° C. Bound IL-6 should be detected by incubation with monoclonal antibody LNI 110-14 after 90 minutes at 37° C. followed by biotin labeled goat anti-routine IgG2b for 90 minutes at 37° C. *Southern Biotechnology*, Birmingham, Ala.). The assays are developed using streptavidin-alkaline phosphatase (*Southern Biotechnology*) and p-nitrophenylphosphate as a substrate and the optical density read at 405 nm.

Disease Activity

The pattern of response for each of the clinical assessments of disease activity are assessed according to typical clinical assessment for SARS. Clinical assessments demonstrate improvement following treatment with thalidomide. Respiratory distress decreases from a median of 2 days at entry to week 6. Similarly, the temperature and other flu like symptoms improve over the period of 24 hours to 3 weeks.

The response data is analyzed for each individual patient. Although the study is primarily designed to assess the short-term effects of TNF inhibitory treatment, follow-up clinical and laboratory data is made available for those patients followed for sufficient time. The duration of response in these patients is defined as the duration of a 20% (or greater) mean improvement in the selected activity measures. Comparison of the clinical and laboratory data for patients treated with infusions of thalidomide (each at 10 mg/kg) compared with those treated with 4 infusions (each at 5 mg/kg) will be used to show differences in the rapidity or extent of response. In patients administered an appropriate dosage of the TNF inhibitor, at least about a 20% decrease in adult respiratory distress syndrome (ARDS) is observed, including each of chronic pulmonary function, diffusion capacity and lung compliance, with adequate patient tolerance. About a 20% decrease in mortality is also observed.

Immunological Investigations and Cytokines

Sera from the patients is also tested for the presence of bioactive TNF, using the WEHI 164 clone 13 cytotoxicity assay (Espevik et al., *J. Imm. Methods* 95:99-105 (1986). Additionally, since production of CRP and SAA are thought to be regulated in large part by IL-6, serum levels of this cytokine are also measured, using 2 different assays, the Medgenix assay and an ELISA, which measure total IL-6.

The invention now being fully described, it will be apparent to one of ordinary skill in the art that many changes and modifications can be made thereto without departing from the spirit or scope of the invention as set forth herein. The foregoing describes the preferred embodiments of the present invention along with a number of possible alternatives. These embodiments, however, are merely for example and the invention is not restricted thereto.

What is claimed is:

1. A method for treating a patient having Severe Acute Respiratory Syndrome (SARS) comprising:
   administering to the patient a therapeutically effective amount of a medicament comprising an inhibitor of TNF and a pharmaceutically acceptable carrier thereof, wherein the medicament is effective against Severe Acute Respiratory Syndrome (SARS).

2. A method for treating a patient having SARS-associated Coronavirus (SARS-CoV) comprising:
   administering to the patient a therapeutically effective amount of a medicament comprising an inhibitor of TNF and a pharmaceutically acceptable carrier thereof, wherein the medicament is effective against SARS-associated Coronavirus (SARS-CoV).

3. A method for treating a patient having Severe Acute Respiratory Syndrome (SARS) comprising: administering to the patent a therapeutically effective amount of an inhibitor of TNF.

4. The method of claim 3, wherein the inhibitor of TNF comprises a soluble recombinant receptor, an antibody, a small molecule that affects the activity of TNF, an antisense oligonucleotide or combinations thereof.

5. The method of claim 3, wherein the inhibitor of TNF inhibits TNF-α.

6. The method, of claim 3, wherein the inhibitor of TNF is etanercept.

7. The method of claim 3, wherein the inhibitor of TNF is an antibody to TNF-α.

8. The method of claim 3, wherein the inhibitor of TNF is a soluble recombinant receptor.

9. The method of claim 8, wherein the inhibitor of TNF is the p75 TNF receptor.

* * * * *